(12) United States Patent
Mizuno et al.

(10) Patent No.: US 8,129,526 B2
(45) Date of Patent: Mar. 6, 2012

(54) PYRIMIDINE COMPOUND AND PESTS CONTROLLING COMPOSITION CONTAINING THE SAME

(75) Inventors: Hajime Mizuno, Toyonaka (JP); Akio Manabe, Sanda (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 154 days.

(21) Appl. No.: 12/579,561

(22) Filed: Oct. 15, 2009

(65) Prior Publication Data

US 2010/0036117 A1 Feb. 11, 2010

Related U.S. Application Data

(63) Continuation of application No. 10/556,337, filed as application No. PCT/JP2004/006586 on May 10, 2004, now Pat. No. 7,732,448.

(30) Foreign Application Priority Data

May 12, 2003 (JP) .................... 2003-132663
Dec. 3, 2003 (JP) .................... 2003-404230

(51) Int. Cl.
*C07D 239/02* (2006.01)
*C07D 401/04* (2006.01)
(52) U.S. Cl. ........................ 544/326; 544/328
(58) Field of Classification Search ................ None
See application file for complete search history.

(56) References Cited

U.S. PATENT DOCUMENTS

| | | | |
|---|---|---|---|
| 2,219,858 A | 10/1940 | Westphal | |
| 3,259,623 A | 7/1966 | Kober et al. | |
| 4,391,810 A | 7/1983 | Hoegerle et al. | |
| 4,752,608 A | 6/1988 | Katoh et al. | |
| 5,250,530 A | 10/1993 | Giencke et al. | |
| 2006/0079533 A1 | 4/2006 | Nieman et al. | |

FOREIGN PATENT DOCUMENTS

| | | |
|---|---|---|
| DE | 40 31 798 A1 | 4/1992 |
| DE | 40 34 762 A1 | 5/1992 |
| EP | 0 056 217 A | 7/1982 |
| HU | 212419 | 6/1996 |
| JP | 57-136576 | 8/1992 |
| WO | 01/07027 A2 | 2/2001 |
| WO | 02/24663 A2 | 3/2002 |

OTHER PUBLICATIONS

Brown et al, Heterocyclic Amplifiers of Phleomycin. IV Pyrimidinylpurines, Phenylpyrimidines and Related Systems with Basic Side Chains, *Australian Journal of Chemistry*, 37(10):2093-2101 (1984).
Brown et al, Pyrimidine Reactions. XXVII Synthesis, Reactivites and Mass Spectra of Some 2-Isopropylpyrimidine Derivatives, *Australian Journal of Chemistry*, 31(6):1391-1395 (1978).
Guy, et al. "Utilization of Polyphosphoric Acid in the Presence of a Co-solvent," Synthesis, Mar. 1980, pp. 222-223.
Maruoka, et al., "Organoaluminum-Promoted Beckmann Rearrangement of Oxime Sulfonates," J. Am. Chem. Soc., 1983, pp. 2831-2843, vol. 105.
Bettoni, et al., "Synthesis and Absolute Configuration of 3-Ethyl and 3-n-Propylpyrrolidine," J. Heterocyclic Chem, 1980, pp. 603-605, vol. 17.
R. Promel et al., "4,5-Dehydropyrimidines," Tetrahedron Letters, No. 26, 1968, pp. 3067-3070.
Declerck et al., "Effets électroniques dans les systèmes hétérocycliques aromatiques spectres de résonance magnétique nucléaire de pyridazines, pyrimidines et s-triazines substituées," Bulletin des Sociétés Chimiques Belges, 1965, 74 (3-4), 119-28, STN record provided.
Hull et al., "Synthetic Antimalarials. Part III. Some Derivatives of Mono- and Di-alkylpyrimidines," Journal of the American Chemical Society, 1946, pp. 357-362.
Zagulyaeva et al., "Relative reactivity of clorine atoms in 2,4-dichloropyrimidine in reactions with ammonia and amines in isooctane and ethanol," Zhurnal Organicheskoi Khimii, 14(2), 1978, Novosibirsk, Russia, pp. 409-413, STN record provided.

*Primary Examiner* — Noble Jarrell
(74) *Attorney, Agent, or Firm* — Sughrue Mion, PLLC

(57) ABSTRACT

The present invention relates to a pyrimidine compound of the formula (II'):

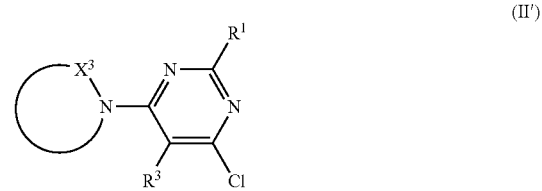

wherein $R^1$ represents a hydrogen atom, halogen atom or C1-C4 alkyl; $R^3$ represents a hydrogen atom, halogen atom or C1-C3 alkyl; $X^3$ represents C5 polymethylene, in which a single $CH_2$—$CH_2$ may be replaced with a single CH=CH, substituted with at least one substituent selected from the group consisting of halogen atoms, trifluoromethyl and C1-C4 alkyls.

5 Claims, No Drawings

PYRIMIDINE COMPOUND AND PESTS CONTROLLING COMPOSITION CONTAINING THE SAME

This application is a continuation of U.S. application Ser. No. 10/556,337, filed Nov. 10, 2005 (now U.S. Pat. No. 7,732,448), which is a National Stage Entry of PCT/JP2004/006586, filed May 10, 2004, which claims benefit of priority under 35 U.S.C. §119 based on Japanese Patent Application Nos. 2003-132663 and 2003-404230, and all of the disclosures of which are hereby incorporated by reference in their entirety.

TECHNICAL FIELD

The present invention relates to a pyrimidine compound and a pests controlling composition containing the same.

BACKGROUND ART

Various compounds have been used in the past for the purpose of pest control. Compounds having a pyrimidine ring are known to have an effect of controlling harmful pests (WO 02/024663). And also a compound having a pyrimidine ring substituted with piperidino is known.

DISCLOSURE OF THE INVENTION

The object of the present invention is to provide a pyrimidine compound having an effect of controlling pests, an pests controlling composition having this pyrimidine compound as an effective ingredient, and a method of controlling pests.

Namely the present invention provides a pyrimidine compound (hereinafter, referred to as the present compound) of the formula (I):

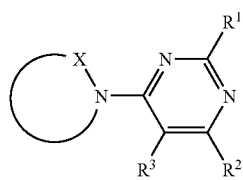

(I)

wherein $R^1$ represents a hydrogen atom, halogen atom or C1-C4 alkyl; $R^2$ represents C3-C7 alkynyloxy; $R^3$ represents a hydrogen atom, halogen atom or C1-C3 alkyl; X represents C4-C7 polymethylene, in which a $CH_2$—$CH_2$ may be replaced with a CH=CH, optionally substituted with at least one substituent selected from the group consisting of halogen atoms, trifluoromethyl and C1-C4 alkyls;
an pests controlling composition containing the present compound as an effective ingredient, and a method of controlling pests comprising applying an effective amount of the present compound to pests or the habitat of pests.
Embodiments of the Invention In this specification, "sec" denotes secondary and "tert" denotes tertiary. The representation of "C3-C7", for example in the "C3-C7 alkynyloxy", means the number of the total carbon atoms in the substituent. "C3-C7 Alkynyloxy" means alkynyloxy in which the number of the total carbon atoms is 3 to 7.

In this specification;
the halogen atom represented by $R^1$ includes, for example, a fluorine atom and chlorine atom;
the C1-C4 alkyl represented by $R^1$ includes, for example, methyl, ethyl, propyl, isopropyl, butyl and isobutyl;
the C3-C7 alkynyloxy represented by $R^2$ includes, for example, C3-C7 alkynyloxy wherein the triple bond is located between the carbons of 2 and 3-position in alkynyl (hereinafter, referred to as C3-C7 2-alkynyloxy), and the C3-C7 2-alkynyloxy include, for example, 2-propynyloxy, 2-butynyloxy, 1-methyl-2-butynyloxy, 2-pentynyloxy, 4,4-dimethyl-2-pentynyloxy, 1-methyl-2-propynyloxy and 1,1-dimethyl-2-propynyloxy; the halogen atom represented by $R^3$ includes, for example, a fluorine atom and chlorine atom;
the C1-C3 alkyl represented by $R^3$ includes, for example, methyl and ethyl.

In the C4-C7 polymethylene, in which a $CH_2$—$CH_2$ may be replaced with a CH=CH, optionally substituted with a halogen atom, trifluoromethyl and C1-C4 alkyl represented by X; the halogen atom includes fluorine atom, chlorine atom and bromine atom; the C1-C4 alkyl includes methyl, ethyl, propyl, isopropyl, isobutyl, sec-butyl and tert-butyl.

In the C4-C7 polymethylene, in which a $CH_2$—$CH_2$ may be replaced with a CH=CH, optionally substituted with at least one substituent selected from the group consisting of halogen atoms, trifluoromethyl and C1-C4 alkyls represented by X, the C4-C7 polymethylene, in which a $CH_2$—$CH_2$ may be replaced with a CH=CH, includes tetramethylene, pentamethylene, hexamethylene, heptamethylene and 2-penten-1,5-ylene.

The C4-C7 polymethylene, in which a $CH_2$—$CH_2$ may be replaced with a CH=CH, optionally substituted with at least one substituent selected from the group consisting of halogen atoms, trifluoromethyl and C1-C4 alkyls represented by X includes C4-C7 polymethylene optionally substituted with at least one substituent selected from the group consisting of halogen atoms, trifluoromethyl and C1-C4 alkyls; and C4-C7 linear alkenylene optionally substituted with at least one substituent selected from the group consisting of halogen atoms, trifluoromethyl and C1-C4 alkyls. The C4-C7 polymethylene optionally substituted with at least one substituent selected from the group consisting of halogen atoms, trifluoromethyl and C1-C4 alkyls includes, for example, C4-C7 polymethylene, C4-C7 polymethylene substituted with a halogen atom(s), C4-C7 polymethylene substituted with trifluoromethyl, C4-C7 polymethylene substituted with a C1-C4 alkyl(s); more specifically it includes tetramethylene, 1-methyltetramethylene, 2-methyltetramethylene, 1-ethyltetramethylene, 1-propyltetramethylene, 1-isopropyltetramethylene, 1-(tert-butyl)tetramethylene, 2-ethyltetramethylene, 1,4-dimethyltetramethylene, 2,3-dimethyltetramethylene, 2,2-dimethyltetramethylene, 2-fluorotetramethylene, 2-(trifluoromethyl)tetramethylene, 3-(trifluoromethyl)tetramethylene, pentamethylene, 1-methylpentamethylene, 2-methylpentamethylene, 3-methylpentamethylene, 1-ethylpentamethylene, 2-ethylpentamethylene, 1-propylpentamethylene, 2-propylpentamethylene, 3-propylpentamethylene, 1-isopropylpentamethylene, 2-isopropylpentamethylene, 3-isopropylpentamethylene, 1-(tert-butyl)pentamethylene, 2-(tert-butyl)pentamethylene, 3-(tert-butyl)pentamethylene, 1-(sec-butyl)pentamethylene, 2-(sec-butyl)pentamethylene, 1,5-dimethylpentamethylene, 1,3-dimethylpentamethylene, 1,4-dimethylpentamethylene, 2,4-dimethylpentamethylene, 1,1-dimethylpentamethylene, 2,2-dimethylpentamethylene, 3,3-dimethylpentamethylene, 2-ethyl-5-methylpentamethylene, 2-ethyl-4-methylpentamethylene, 2,4-diethylpentamethylene, 1,2-dimethylpentamethylene, 2,2,4-trimethylpentamethylene, 1,2,4,5-tetramethylpentamethylene, 2,2,4,4-tetramethylpentamethylene, 2-fluoropentamethylene, 2-chloropentamethylene, 2-bromopentamethylene, 3-fluoropentamethylene, 3-chloropentamethylene, 3-bromopentamethylene, 2,2-difluoropentamethylene, 3,3-difluoropentamethylene, 2-fluoro-2-methylpentamethylene, 1-(trifluoromethyl)pentamethylene, 2-(trifluoromethyl)pentamethylene, 3-(trifluoromethyl)pentamethylene, hexamethylene, 1-methylhexamethylene, 2-methylhexamethylene, 3-methylhexamethylene, 4-methylhexamethylene, 1-ethylhexamethylene, 2-ethylhexamethylene, 3-ethylhexamethylene, 1-propylhexamethylene, 2-propylhexamethylene, 3-propylhexamethylene, 1-isopropylhexamethylene, 2-isopropylhexamethylene, 3-isopropylhexamethylene, 1-(tert-butyl)hexamethylene, 1-isobutylhexamethylene, 1-(trifluoromethyl)hexamethylene, 1,4-dimethylhexamethylene, 1,5-dimethylhexamethylene, 1,6-dimethylhexamethylene, 2,5-dimethylhexamethylene and heptamethylene.

The C4-C7 linear alkenylene optionally substituted with at least one substituent selected from the group consisting of halogen atoms, trifluoromethyl and C1-C4 alkyls, for example, 2-buten-1,4-ylene, 2-methyl-2-buten-1,4-ylen, 2,3-dimethyl-2-buten-1,4-ylen, 2-penten-1,5-ylene, 1-ethyl-2-penten-1,5-ylene, 2-methyl-2-penten-1,5-ylene, 2-ethyl-2-penten-1,5-ylene, 4-methyl-2-penten-1,5-ylene, 5-methyl-2-penten-1,5-ylene, 5-ethyl-2-penten-1,5-ylene, 2,4-dimethyl-2-penten-1,5-ylene, 2-hexen-1,6-ylene, 1-methyl-2-hexen-1,6-ylene, 1-ethyl-2-hexen-1,6-ylene, 2-methyl-2-hexen-1,6-ylene, 6-ethyl-2-hexen-1,6-ylene, 2,5-dimethyl-2-hexen-1,6-ylene, 3-hexen-1,6-ylene, 2-hepten-1,7-ylene and 3-hepten-1,7-ylene.

Embodiments of the present compound include, for example, the following compounds:

the pyrimidine compound wherein $R^1$ is a hydrogen atom or C1-C4 alkyl in the formula (I);

the pyrimidine compound wherein $R^1$ is a hydrogen atom in the formula (I);

the pyrimidine compound wherein $R^2$ is C3-C7 2-alkynyloxy in the formula (I);

the pyrimidine compound wherein $R^2$ is 2-butynyloxy or 2-pentynyloxy in the formula (I);

the pyrimidine compound wherein $R^3$ is a hydrogen atom in the formula (I);

the pyrimidine compound wherein $R^2$ is a halogen atom in the formula (I);

the pyrimidine compound wherein $R^2$ is a fluorine atom in the formula (I);

the pyrimidine compound wherein X is C4-C7 polymethylene optionally substituted with at least one substituent selected from the group consisting of halogen atoms, trifluoromethyl and C1-C4 alkyl in the formula (I);

the pyrimidine compound wherein X is C4-C7 polymethylene optionally substituted with a halogen atom, trifluoromethyl or C1-C4 alkyl in the formula (I);

the pyrimidine compound wherein X is C4-C7 polymethylene in the formula (I);

the pyrimidine compound wherein X is C4-C7 polymethylene substituted with a halogen atom(s) in the formula (I);

the pyrimidine compound wherein X is C4-C7 polymethylene substituted with a trifluoromethyl in the formula (I);

the pyrimidine compound wherein X is C4-C7 polymethylene substituted with a C1-C4 alkyl(s) in the formula (I);

the pyrimidine compound wherein X is tetraethylene or pentamethylene, optionally substituted with at least one substituent selected from the group consisting of halogen atoms, trifluoromethyl and C1-C4 alkyls in the formula (I);

the pyrimidine compound wherein X is C4-C7 linear alkenylene optionally substituted with at least one substituent selected from the group consisting of halogen atoms, trifluoromethyl and C1-C4 alkyls in the formula (I);

the pyrimidine compound wherein X is tetramethylene optionally substituted with at least one substituent selected from the group consisting of halogen atoms, trifluoromethyl and C1-C4 alkyls in the formula (I);

the pyrimidine compound wherein X is pentamethylene optionally substituted with at least one substituent selected from the group consisting of halogen atoms, trifluoromethyl and C1-C4 alkyls in the formula (I);

the pyrimidine compound wherein X is hexamethylene optionally substituted with at least one substituent selected from the group consisting of halogen atoms, trifluoromethyl and C1-C4 alkyls in the formula (I);

the pyrimidine compound wherein X is tetramethylene optionally substituted with a halogen atom, trifluoromethyl or C1-C4 alkyl in the formula (I);

the pyrimidine compound wherein X is pentamethylene optionally substituted with a halogen atom, trifluoromethyl or C1-C4 alkyl in the formula (I);

the pyrimidine compound wherein X is hexamethylene optionally substituted with a halogen atom, trifluoromethyl or C1-C4 alkyl in the formula (I);

the pyrimidine compound wherein X is tetramethylene optionally substituted with a halogen atom, trifluoromethyl or C1-C4 alkyl in the formula (I);

the pyrimidine compound wherein X is pentamethylene optionally substituted with a halogen atom, trifluoromethyl or C1-C4 alkyl in the formula (I);

the pyrimidine compound wherein X is hexamethylene optionally substituted with a halogen atom, trifluoromethyl or C1-C4 alkyl in the formula (I);

the pyrimidine compound wherein X is tetramethylene in the formula (I), following described;

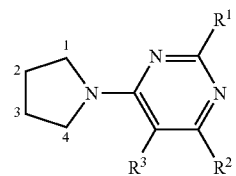

the pyrimidine compound wherein X is pentamethylene in the formula (I), following described;

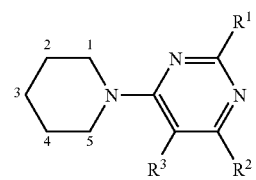

the pyrimidine compound wherein X is hexamethylene in the formula (I), following described;

the pyrimidine compound wherein X is heptamethylene in the formula (I), following described;

the pyrimidine compound wherein $R^1$ is a hydrogen atom or C1-C4 alkyl, and X is C4-C7 polymethylene optionally substituted with at least one substituent selected from the group consisting of halogen atoms, trifluoromethyl and C1-C4 alkyls in the formula (I);

the pyrimidine compound wherein $R^1$ is a hydrogen atom or C1-C4 alkyl, and X is C4-C7 polymethylene optionally substituted with a halogen atom, trifluoromethyl or C1-C4 alkyl in the formula (I);

the pyrimidine compound wherein $R^1$ is a hydrogen atom or C1-C4 alkyl, and X is tetraethylene or pentamethylene, optionally substituted with at least one substituent selected from the group consisting of halogen atoms, trifluoromethyl and C1-C4 alkyls in the formula (I);

the pyrimidine compound wherein $R^1$ is a hydrogen atom or C1-C4 alkyl, and X is C4-C7 linear alkenylene optionally substituted with at least one substituent selected from the group consisting of halogen atoms, trifluoromethyl and C1-C4 alkyls in the formula (I);

the pyrimidine compound wherein $R^2$ is 2-butynyloxy or 2-pentynyloxy, and X is C4-C7 polymethylene optionally substituted with at least one substituent selected from the group consisting of halogen atoms, trifluoromethyl and C1-C4 alkyls in the formula (I);

the pyrimidine compound wherein $R^2$ is 2-butynyloxy or 2-pentynyloxy, and X is C4-C7 polymethylene optionally substituted with a halogen atom, trifluoromethyl or C1-C4 alkyl in the formula (I);

the pyrimidine compound wherein $R^2$ is 2-butynyloxy or 2-pentynyloxy, and X is tetraethylene or pentamethylene, optionally substituted with at least one substituent selected from the group consisting of halogen atoms, trifluoromethyl and C1-C4 alkyls in the formula (I);

the pyrimidine compound wherein $R^2$ is 2-butynyloxy or 2-pentynyloxy, and X is C4-C7 linear alkenylene optionally substituted with at least one substituent selected from the group consisting of halogen atoms, trifluoromethyl and C1-C4 alkyls in the formula (I);

the pyrimidine compound wherein $R^1$ is a hydrogen atom or C1-C4 alkyl, $R^2$ is 2-butynyloxy or 2-pentynyloxy, and X is C4-C7 polymethylene optionally substituted with at least one substituent selected from the group consisting of halogen atoms, trifluoromethyl and C1-C4 alkyls in the formula (I);

the pyrimidine compound wherein $R^1$ is a hydrogen atom or C1-C4 alkyl, $R^2$ is 2-butynyloxy or 2-pentynyloxy, and X is C4-C7 polymethylene optionally substituted with a halogen atom, trifluoromethyl or C1-C4 alkyl in the formula (I);

the pyrimidine compound wherein $R^1$ is a hydrogen atom or C1-C4 alkyl, $R^2$ is 2-butynyloxy or 2-pentynyloxy, and X is tetraethylene or pentamethylene, optionally substituted with at least one substituent selected from the group consisting of halogen atoms, trifluoromethyl and C1-C4 alkyls in the formula (I);

the pyrimidine compound wherein $R^1$ is a hydrogen atom or C1-C4 alkyl, $R^2$ is 2-butynyloxy or 2-pentynyloxy, and X is C4-C7 linear alkenylene optionally substituted with at least one substituent selected from the group consisting of halogen atoms, trifluoromethyl and C1-C4 alkyls in the formula (I);

the pyrimidine compound wherein $R^1$ is a hydrogen atom, and $R^3$ is a hydrogen atom in the formula (I);

the pyrimidine compound wherein $R^1$ is a hydrogen atom, and $R^3$ is a halogen atom in the formula (I);

the pyrimidine compound wherein $R^1$ is a hydrogen atom, and $R^3$ is a fluorine atom in the formula (I);

the pyrimidine compound wherein $R^1$ is a hydrogen atom, $R^2$ is C3-C7 2-alkynyloxy, and $R^3$ is a hydrogen atom in the formula (I);

the pyrimidine compound wherein $R^1$ is a hydrogen atom, $R^2$ is C3-C7 2-alkynyloxy, and $R^3$ is a halogen atom in the formula (I);

the pyrimidine compound wherein $R^1$ is a hydrogen atom, $R^2$ is C3-C7 2-alkynyloxy, and $R^3$ is a fluorine atom in the formula (I);

the pyrimidine compound wherein $R^1$ is a hydrogen atom, $R^2$ is C3-C7 2-alkynyloxy, $R^3$ is a hydrogen atom, and X is C3-C8 pentamethylene optionally substituted with at least one substituent selected from the group consisting of halogen atoms, trifluoromethyl and C1-C4 alkyls in the formula (I);

the pyrimidine compound wherein $R^1$ is a hydrogen atom, $R^2$ is C3-C7 2-alkynyloxy, $R^3$ is a halogen atom, and X is C3-C8 pentamethylene optionally substituted with at least one substituent selected from the group consisting of halogen atoms, trifluoromethyl and C1-C4 alkyls in the formula (I);

the pyrimidine compound wherein $R^1$ is a hydrogen atom, $R^2$ is C3-C7 2-alkynyloxy, $R^3$ is a fluorine atom, and X is C3-C8 pentamethylene optionally substituted with at least one substituent selected from the group consisting of halogen atoms, trifluoromethyl and C1-C4 alkyls in the formula (I);

the pyrimidine compound wherein $R^1$ is a hydrogen atom, $R^2$ is C3-C7 2-alkynyloxy, $R^3$ is a hydrogen atom, and X is C3-C8 hexamethylene optionally substituted with at least one substituent selected from the group consisting of halogen atoms, trifluoromethyl and C1-C4 alkyls in the formula (I);

the pyrimidine compound wherein $R^1$ is a hydrogen atom, $R^2$ is C3-C7 2-alkynyloxy, $R^3$ is a halogen atom, and X is C3-C8 hexamethylene optionally substituted with at least one substituent selected from the group consisting of halogen atoms, trifluoromethyl and C1-C4 alkyls in the formula (I);

the pyrimidine compound wherein $R^1$ is a hydrogen atom, $R^2$ is C3-C7 2-alkynyloxy, $R^3$ is a fluorine atom, and X is C3-C8 hexamethylene optionally substituted with at least one substituent selected from the group consisting of halogen atoms, trifluoromethyl and C1-C4 alkyls in the formula (I);

the pyrimidine compound wherein $R^1$ is a hydrogen atom, $R^2$ is C3-C7 2-alkynyloxy, $R^3$ is a hydrogen atom, and X is C3-C8 pentamethylene optionally substituted with a halogen atom, trifluoromethyl or C1-C4 alkyl in the formula (I);

the pyrimidine compound wherein $R^1$ is a hydrogen atom, $R^2$ is C3-C7 2-alkynyloxy, $R^3$ is a halogen atom, and X is C3-C8 pentamethylene optionally substituted with a halogen atom, trifluoromethyl or C1-C4 alkyl in the formula (I);

the pyrimidine compound wherein $R^1$ is a hydrogen atom, $R^2$ is C3-C7 2-alkynyloxy, $R^3$ is a fluorine atom, and X is C3-C8 pentamethylene optionally substituted with a halogen atom, trifluoromethyl or C1-C4 alkyl in the formula (I);

the pyrimidine compound wherein $R^1$ is a hydrogen atom, $R^2$ is C3-C7 2-alkynyloxy, $R^3$ is a hydrogen atom, and X is C3-C8 hexamethylene optionally substituted with a halogen atom, trifluoromethyl or C1-C4 alkyl in the formula (I);

the pyrimidine compound wherein $R^1$ is a hydrogen atom, $R^2$ is C3-C7 2-alkynyloxy, $R^3$ is a halogen atom, and X is C3-C8 hexamethylene optionally substituted with a halogen atom, trifluoromethyl or C1-C4 alkyl in the formula (I);

the pyrimidine compound wherein $R^1$ is a hydrogen atom, $R^2$ is C3-C7 2-alkynyloxy, $R^3$ is a fluorine atom, and X is C3-C8 hexamethylene optionally substituted with a halogen atom, trifluoromethyl or C1-C4 alkyl in the formula (I).

The production method of the present invention will be illustrated below.

The present compound can be produced, for example, by the production method 1 and 2 described below.

Production Method 1

The compound of the formula (I) can be produced by making a compound of the formula (II) react with a compound of the formula (III) in the presence of a base.

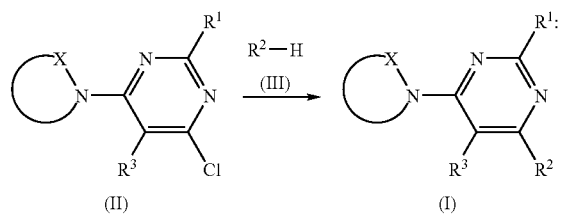

wherein $R^1$, $R^2$, $R^3$ and X are as defined above.

This reaction is usually carried out in a solvent.

As the solvent used in the reaction, there are listed, for example, ethers such as tetrahydrofuran, diethyl ether, tert-butyl methyl ether, ethylene glycol dimethyl ether and 1,4-dioxane, acid amides such as N,N-dimethyl formamide, nitrites such as acetonitrile, sulfoxides such as dimethyl sulfoxide, hydrocarbons such as hexane, aromatic hydrocarbons such as benzene and toluene, and the mixture thereof.

As the base used in the reaction, there are listed, for example, alkali metal hydride such as sodium hydride and potassium hydride, carbonate such as potassium carbonate, alkali metal alkoxide such as potassium tert-butoxide and sodium tert-butoxide.

The amount of the compound of the formula (III) is usually 1 to 2 moles, and the amount of the base is usually 1 to 2 mole, based on one mol of the compound of the formula (II).

The reaction temperature of the reaction is usually in the range from 0 to 80° C., and the reaction time is usually in the range from 0.5 to 12 hours.

After completion of the reaction, the compound of the formula (I) can be isolated by the procedure such as extracting the reaction mixture into an organic solvent, drying, and concentrating. The isolated compound of the formula (I) can be further purified by chromatography, re-crystallization and the like.

Production Method 2

The compound of the formula (I) can be produced by making a compound of the formula (IV) react with a compound of the formula (V) or its salt such as a hydrochloride of the compound of the formula (V).

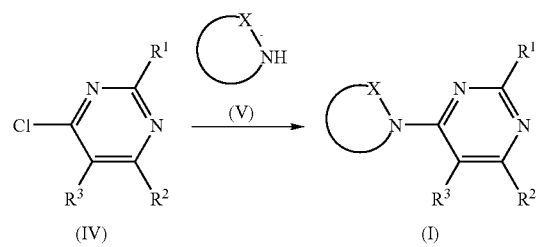

wherein $R^1$, $R^2$, $R^3$ and X are as defined above.

This reaction is usually carried out in a solvent, and optionally carried out in the presence of a base.

As the solvent used in the reaction, there are listed, for example, ethers such as tetrahydrofuran, diethyl ether, tert-butyl methyl ether, ethylene glycol dimethyl ether and 1,4-dioxane, acid amides such as N,N-dimethyl formamide, nitrites such as acetonitrile, alcohols such as methanol and ethanol, hydrocarbons such as hexane, aromatic hydrocarbons such as benzene and toluene, and the mixture thereof.

As the base used in the reaction, there are listed, for example, alkali metal hydride such as sodium hydride and potassium hydride, carbonate such as potassium carbonate, tertiary amines such as triethylamine and ethyldiisopropylamine.

The amount of the compound of the formula (V) is usually 1 to 3 moles based on one mol of the compound of the formula (IV). When the reaction is carried out in the presence of the base, the amount of base is usually 1 to 4 moles, based on one mol of the compound of the formula (IV).

The reaction temperature of the reaction is usually in the range from 0 to 150° C., and the reaction time is usually in the range from 0.1 to 48 hours.

After completion of the reaction, the compound of the formula (I) can be isolated by the following procedure:

(i) extracting the reaction mixture into an organic solvent, drying and concentrating;

(ii) concentrating the reaction mixture as it is.

The isolated compound of the formula (I) can be further purified by chromatography, re-crystallization and the like.

Next, the production methods of the intermediates of the present compound will be illustrated below.

Reference Production Method 1

The compound of the formula (II) can be produced by making a compound of the formula (VI) react with a compound of the formula (V) or its salt such as a hydrochloride of the compound of the formula (V).

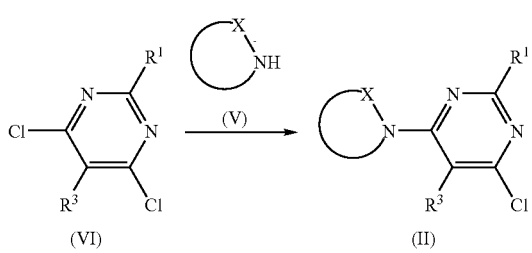

wherein $R^1$, $R^2$, $R^3$ and X are as defined above.

This reaction is usually carried out in a solvent, and optionally carried out in the presence of a base.

As the solvent used in the reaction, there are listed, for example, ethers such as tetrahydrofuran, diethyl ether, tert-butyl methyl ether, ethylene glycol dimethyl ether and 1,4-dioxane, acid amides such as N,N-dimethyl formamide, nitrites such as acetonitrile, alcohols such as methanol and ethanol, hydrocarbons such as hexane, aromatic hydrocarbons such as benzene and toluene, sulfoxide such as dimethyl sulfoxide, and the mixture thereof.

As the base used in the reaction, there are listed, for example, alkali metal hydride such as sodium hydride and potassium hydride, carbonate such as potassium carbonate, alkali metal hydroxide such as potassium tert-butoxide and sodium tert-butoxide.

The amount of the compound of the formula (VI) is usually 1 to 3 moles based on one mol of the compound of the formula (V). When the reaction is carried out in the presence of the base, the amount of base is usually 1 to 4 moles based on one mol of the compound of the formula (V).

The reaction temperature of the reaction is usually in the range from 0 to 150° C., and the reaction time is usually in the range from 0.1 to 48 hours.

After completion of the reaction, the compound of the formula (II) can be isolated by the following procedure:

(i) extracting the reaction mixture into an organic solvent, drying and concentrating;

(ii) concentrating the reaction mixture as it is.

The isolated compound of the formula (II) can be further purified by chromatography, re-crystallization and the like.

The compounds of the formula (II) includes, for example, the following compounds:

the compound wherein X is C4-C7 polymethylene in the formula (II); the compound of the formula (II'):

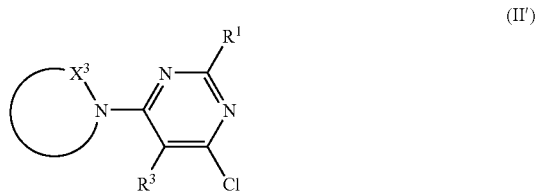

wherein $R^1$ represents a hydrogen atom, halogen atom or C1-C4 alkyl; $R^3$ represents a hydrogen atom, halogen atom or C1-C3 alkyl; $X^3$ represents C4-C7 polymethylene, in which a $CH_2$—$CH_2$ may be replaced with a CH=CH, substituted with at least one substituent selected from the group consisting of halogen atoms, trifluoromethyl and C1-C4 alkyls;

the compound wherein $X^3$ is C4-C7 polymethylene substituted with at least one substituent selected from the group consisting of halogen atoms, trifluoromethyl and C1-C4 alkyls in the formula (II');

the compound wherein $X^3$ is C4-C7 polymethylene substituted with a halogen atom(s) in the formula (II');

the compound wherein $X^3$ is C4-C7 polymethylene substituted with a trifluoromethyl in the formula (II');

the compound wherein $X^3$ is C4-C7 polymethylene substituted with a C1-C4 alkyl(s) in the formula (II').

Reference Production Method 2

The compound of the formula (IV) can be produced by making a compound of the formula (VI) react with a compound of the formula (III) in the presence of a base.

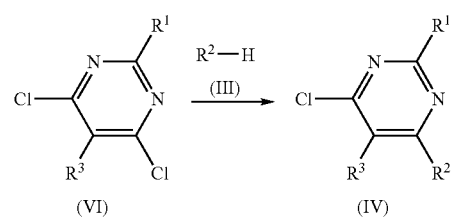

wherein $R^1$, $R^2$, $R^3$ and X are as defined above.

This reaction is usually carried out in a solvent, and optionally carried out in the presence of a base.

As the solvent used in the reaction, there are listed, for example, ethers such as tetrahydrofuran, diethyl ether, tert-butyl methyl ether, ethylene glycol dimethyl ether and 1,4-dioxane, acid amides such as N,N-dimethyl formamide, nitrites such as acetonitrile, hydrocarbons such as hexane, aromatic hydrocarbons such as benzene and toluene, sulfoxide such as dimethyl sulfoxide, and the mixture thereof.

As the base used in the reaction, there are listed, for example, alkali metal hydride such as sodium hydride and potassium hydride, carbonate such as potassium carbonate, alkali metal hydroxide such as potassium tert-butoxide and sodium tert-butoxide.

The amount of the compound of the formula (III) is usually 1 to 2 moles, and the amount of the base is usually 1 to 2 moles, based on one mol of the compound of the formula (IV).

The reaction temperature of the reaction is usually in the range from −20 to 80° C., and the reaction time is usually in the range from 0.5 to 12 hours.

After completion of the reaction, the compound of the formula (IV) can be isolated by the procedure such as extracting the reaction mixture into an organic solvent, drying and concentrating.

The isolated compound of the formula (IV) can be further purified by chromatography, re-crystallization and the like.

The compounds of the formula (IV) includes, for example, the following compounds:

the compound wherein $R^1$ is a hydrogen atom or C1-C4 alkyl in the formula (IV);

the compound wherein $R^1$ is a hydrogen atom in the formula (II);

the compound wherein $R^2$ is 2-butynyloxy or 2-pentynyloxy in the formula (IV).

Reference Production Method 3

The compound of the formula (V') can be produced, for example, from a compound of the formula (IX) by the following scheme.

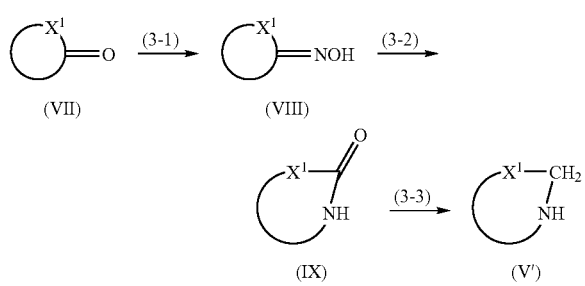

wherein $X^1$ represents C3-C6 polymethylene optionally substituted with at least one substituent selected from the group consisting of halogen atoms, trifluoromethyl and C1-C4 alkyls.

Process 3-1

The compound of the formula (VII) can be produced by making a compound of the formula (VII) react with a hydroxy amine in a solvent.

This reaction is usually carried out in a solvent, and optionally carried out in the presence of a base.

As the solvent used in the reaction, there are listed, for example, ethers such as tetrahydrofuran, diethyl ether, tert-butyl methyl ether, ethylene glycol dimethyl ether and 1,4-dioxane, acid amides such as N,N-dimethyl formamide, alcohols such as methanol and ethanol, water, and the mixture thereof.

As the base used in the reaction, there are listed, for example, inorganic base such as sodium hydroxide and potassium hydroxide, tertiary amines such as triethylamine, and nitrogen containing aromatics such as pyridine.

The amount of hydroxylamine or its salt is usually 1 to 3 mole, and the amount of the base is 1 to 5 moles, based on one mol of the compound of the formula (VII).

The reaction temperature of the reaction is usually in the range from 0 to 80° C., and the reaction time is usually in the range from 1 to 24 hours.

After completion of the reaction, the compound of the formula (VIII) can be isolated by the procedure such as extracting the reaction mixture into an organic solvent, drying and concentrating.

The isolated compound of the formula (VIII) can be further purified by chromatography, re-crystallization and the like.

The compound of the formula (IX) is the compound disclosed, for example, in Synthesis, (1980), p. 222-223, or J. Am. Chem. Soc., (1983), 105, p. 2381-2843; or can be produced by the following process.

Process 3-2

The compound of the formula (IX) can be produced by making a compound of the formula (VIII) react in the presence of the reagent for the rearrangement reaction.

This reaction is usually carried out in a solvent.

As the solvent used in the reaction, there are listed, for example, acid amides such as N,N-dimethyl formamide, aromatic hydrocarbons such as toluene and benzen, and the mixture thereof.

As the reagent for the rearrangement reaction, there are listed chlorides of phosphorous such as phosphorous oxychloride, chlorides of sulfur such as thionyl chloride, and poly phosphoric acid.

The amount of the reagent of the rearrangement reaction is usually 0.1 mole to excess amount based on one mole of the compound of the formula (VIII).

The reaction temperature of the reaction is usually in the range from 0 to 150° C., and the reaction time is usually in the range from 0.1 to 48 hours.

After completion of the reaction, the compound of the formula (VIII) can be isolated by the procedure such as extracting the reaction mixture into an organic solvent, drying and concentrating.

The isolated compound of the formula (VIII) can be further purified by chromatography, re-crystallization and the like.

The compound of the formula (V') is the compound disclosed, for example, in J. Am. Chem. Soc., (1983), 105, p. 2381-2843 or J. Heterocyclic. Chem., (1980)17, p. 603; or can be produced by the following process.

Process 3-3

The compound of the formula (V') can be produced by making a compound of the formula (IX) react with the reducing reagent.

This reaction is usually carried out in a solvent.

As the solvent used in the reaction, there are listed, for example, ethers such as tetrahydrofuran and diethyl ether.

As the reducing reagent, there are listed hydrides of aluminum such as lithium aluminium hydride.

The amount of the reducing reagent is usually 0.5 to 6 moles based on one mole of the compound of the formula (IX).

The reaction temperature of the reaction is usually in the range from 0 to 120° C., and the reaction time is usually in the range from 1 to 24 hours.

After completion of the reaction, the compound of the formula (V') can be isolated by the following procedure:

(i) poring successively water, aqueous solution of 15% sodium hydroxide, and water into the reaction mixture, extracting into an organic solvent, drying and concentrating; when necessary, distilling;

(ii) poring successively water, aqueous solution of 15% sodium hydroxide, and water into the reaction mixture, extracting into an organic solvent, drying, and collecting the hydrochloric salts of the compound of the formula (V') by stirring in the presence of hydrogen chloride or hydrochloric acid.

Reference Production Method 4

The compound of the formula (V") can be produced, for example, from a compound of the formula (IX) by the following scheme.

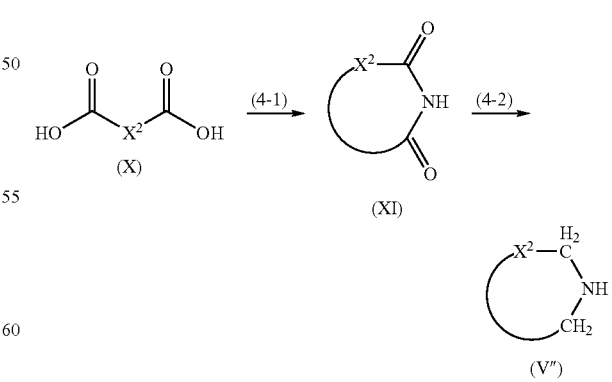

wherein $X^2$ represents C2-C5 polymethylene optionally substituted with at least one substituent selected from the group consisting of halogen atoms, trifluoromethyl and C1-C4 alkyls.

Process 4-1

The compound of the formula (XI) can be produced by making a compound of the formula (X) react with urea.

This reaction is usually carried out in absence of a solvent.

The amount of urea is usually 10 moles to excess amount based one mole of the compound of the formula (X).

The reaction temperature of the reaction is usually in the range from 50 to 170° C., and the reaction time is usually in the range from 1 to 24 hours.

After completion of the reaction, the compound of the formula (XI) can be isolated by the procedure such as extracting the reaction mixture into an organic solvent, drying and concentrating.

The isolated compound of the formula (XI) can be further purified by chromatography, re-crystallization and the like.

Process 4-2

The compound of the formula (V") can be produced by making a compound of the formula (XI) react with the reducing reagent.

This reaction is usually carried out in a solvent.

As the solvent used in the reaction, there are listed, for example, ethers such as tetrahydrofuran and diethyl ether.

As the reducing reagent, there are listed hydrides of aluminum such as lithium aluminium hydride.

The amount of the reducing reagent is usually 1 to 6 moles based on one mole of the compound of the formula (XI).

The reaction temperature of the reaction is usually in the range from 0 to 120° C., and the reaction time is usually in the range from 1 to 24 hours.

After completion of the reaction, the compound of the formula (V) can be isolated by the following procedure:

(i) poring successively water, aqueous solution of 15% sodium hydroxide, and water into the reaction mixture, extracting into an organic solvent, drying and concentrating; when necessary, distilling;

(ii) poring successively water, aqueous solution of 15% sodium hydroxide, and water into the reaction mixture, extracting into an organic solvent, drying, and collecting the hydrochloric salts of the compound of the formula (V") by stirring in the presence of hydrogen chloride or hydrochloric acid.

Next, the specific examples of the present compounds are showing below.

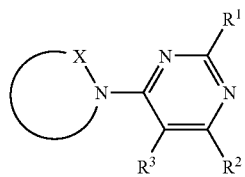

(I)

The pyrimidine compound wherein $R^1$ is a hydrogen atom, $R^2$ is 2-propynyloxy, $R^3$ is a hydrogen atom, X is one selected from the group (A) below.

Group (A):

tetramethylene, 1-methyltetramethylene, 1-ethyltetramethylene, 1-propyltetramethylene, 1-isopropyltetramethylene, 1-(tert-butyl)tetramethylene, 1,4-dimethyltetramethylene, 2-(trifluoromethyl)tetramethylene, 3-(trifluoromethyl)tetramethylene, pentamethylene, 1-methylpentamethylene, 2-methylpentamethylene, 3-methylpentamethylene, 1-ethylpentamethylene, 2-ethylpentamethylene, 1-propylpentamethylene, 2-propylpentamethylene, 3-propylpentamethylene, 3-isopropylpentamethylene, 1-(tert-butyl) pentamethylene, 3-(tert-butyl)pentamethylene, 1-(sec-butyl)pentamethylene, 1,5-dimethylpentamethylene, 1,3-dimethylpentamethylene, 1,4-dimethylpentamethylene, 2,2-dimethylpentamethylene, 3,3-dimethylpentamethylene, 2-ethyl-5-methylpentamethylene, 2-fluoropentamethylene, 3-fluoropentamethylene, 2,2-difluoropentamethylene, 3,3-difluoropentamethylene, 1-(trifluoromethyl) pentamethylene, 2-(trifluoromethyl)pentamethylene, 3-(trifluoromethyl)pentamethylene, hexamethylene, 1-methylhexamethylene, 2-methylhexamethylene, 3-methylhexamethylene, 1-ethylhexamethylene, 2-ethylhexamethylene, 3-ethylhexamethylene, 1-propylhexamethylene, 1-isopropylhexamethylene, 1-(tert-butyl) hexamethylene, 1-isobutylhexamethylene, 1,4-dimethylhexamethylene group, 1,5-dimethylhexamethylene, 1,6-dimethylhexamethylene, 2,5-dimethylhexamethylene, 1-(trifluoromethyl)hexamethylene, heptamethylene, 2-penten-1,5-ylene and 2,4-dimethyl-2-penten-1,5-ylene.

The pyrimidine compound wherein $R^1$ is a hydrogen atom, $R^2$ is 2-butynyloxy, $R^3$ is methyl, X is one selected from the group (B) below.

Group (B):

tetramethylene, 1-methyltetramethylene, 1-ethyltetramethylene, 1,4-dimethyltetramethylene, 2-(trifluoromethyl)tetramethylene 3-(trifluoromethyl)tetramethylene, pentamethylene, 1-methylpentamethylene, 2-methylpentamethylene, 3-methylpentamethylene, 1-ethylpentamethylene, 2-ethylpentamethylene, 1,5-dimethylpentamethylene, 1,3-dimethylpentamethylene, 1,4-dimethylpentamethylene, 2,2-dimethylpentamethylene, 3,3-dimethylpentamethylene, 2-ethyl-5-methylpentamethylene, 1-(trifluoromethyl)pentamethylene, 2-(trifluoromethyl)pentamethylene, 3-(trifluoromethyl)pentamethylene, hexamethylene, 1-methylhexamethylene, 2-methylhexamethylene, 3-methylhexamethylene, 1-ethylhexamethylene, 2-ethylhexamethylene, 3-ethylhexamethylene, 1-(trifluoromethyl)hexamethylene, heptamethylene, 2-penten-1,5-ylene and 2,4-dimethyl-2-penten-1,5-ylene.

The pyrimidine compound wherein $R^1$ is a hydrogen atom, $R^2$ is 2-propynyloxy, $R^3$ is a fluorine atom, X is one selected from the group (A) above.

The pyrimidine compound wherein $R^1$ is a hydrogen atom, $R^2$ is 2-propynyloxy, $R^3$ is a chlorine atom, X is one selected from the group (B) above.

The pyrimidine compound wherein $R^1$ is a hydrogen atom, $R^2$ is 1-methyl-2-propynyloxy, $R^3$ is a chlorine atom, X is one selected from the group (B) above.

The pyrimidine compound wherein $R^1$ is a hydrogen atom, $R^2$ is 2-pentynyloxy, $R^3$ is a hydrogen atom, X is one selected from the group (C) below.

Group (C):

tetramethylene, 1-methyltetramethylene, 2-methyltetramethylene, 1-ethyltetramethylene, 1-propyltetramethylene, 1-isopropyltetramethylene, 1-(tert-butyl)tetramethylene, 2-ethyltetramethylene, 1,4-dimethyltetramethylene, 2,3-dimethyltetramethylene, 2,2-dimethyltetramethylene, 2-fluorotetramethylene, 2-(trifluoromethyl)tetramethylene, 3-(trifluoromethyl)tetramethylene, pentamethylene, 1-methylpentamethylene, 2-methylpentamethylene, 3-methylpentamethylene, 1-ethylpentamethylene, 2-ethylpentamethylene, 1-propylpentamethylene, 2-propylpentamethylene, 3-propylpentamethylene, 1-isopropylpentamethylene, 2-isopropylpentamethylene, 3-isopropylpentamethylene, 1-(tert-butyl)pentamethylene, 2-(tert-butyl)pentamethylene, 3-(tert-butyl)pentamethylene, 1-(sec-butyl)pentamethylene, 2-(sec-butyl)pentamethylene, 1,5-dimethylpentamethylene, 1,3-dimethylpentamethylene, 1,4-dimethylpentamethylene, 2,4-dimethylpentamethylene, 1,1-dimethylpentamethylene, 2,2-dimethylpentamethylene, 3,3-dimethylpentamethylene, 2-ethyl-4-methylpentamethylene, 2-ethyl-5-methylpentamethylene, 2,4-diethylpentamethylene, 2-fluoropentamethylene, 2-chloropentamethylene, 2-bromopentamethylene, 3-fluoropentamethylene, 3-chloropentamethylene, 3-bromopentamethylene, 2,2-difluoropentamethylene, 3,3-difluoropentamethylene, 2-fluoro-2-methylpentamethylene, 1-(trifluoromethyl)pentamethylene, 2-(trifluoromethyl)pentamethylene, 3-(trifluoromethyl)pentamethylene, hexamethylene, 1-methylhexamethylene, 2-methylhexamethylene, 3-methylhexamethylene, 1-ethylhexamethylene, 2-ethylhexamethylene, 3-ethylhexamethylene, 1-propylhexamethylene, 2-propylhexamethylene, 3-propylhexamethylene, 1-isopropylhexamethylene, 2-isopropylhexamethylene, 3-isopropylhexamethylene, 1-(tert-butyl)hexamethylene, 1-isobutylhexamethylene, 1,4-dimethylhexamethylene group, 1,5-dimethylhexamethylene, 1,6-dimethylhexamethylene, 2,5-dimethylhexamethylene, 1-(trifluoromethyl)hexamethylene, heptamethylene, 2-penten-1,5-ylene and 2,4-dimethyl-2-penten-1,5-ylene.

The pyrimidine compound wherein $R^1$ is a hydrogen atom, $R^2$ is 2-pentynyloxy, $R^3$ is methyl, X is one selected from the group (B) above.

The pyrimidine compound wherein $R^1$ is a hydrogen atom, $R^2$ is 2-pentynyloxy, $R^3$ is a fluorine atom, X is one selected from the group (C) above.

The pyrimidine compound wherein $R^1$ is a hydrogen atom, $R^2$ is 2-pentynyloxy, $R^3$ is a chlorine atom, X is one selected from the group (A) above.

The pyrimidine compound wherein $R^1$ is a hydrogen atom, $R^2$ is 2-butynyloxy, $R^3$ is a hydrogen atom, X is one selected from the group (C) above.

The pyrimidine compound wherein $R^1$ is a hydrogen atom, $R^2$ is 2-butynyloxy, $R^3$ is a fluorine atom, X is one selected from the group (C) above.

The pyrimidine compound wherein $R^1$ is a hydrogen atom, $R^2$ is 2-butynyloxy, $R^3$ is a chlorine atom, X is one selected from the group (A) above.

The pyrimidine compound wherein $R^1$ is a hydrogen atom, $R^2$ is 1-methyl-2-propynyloxy, $R^3$ is a hydrogen atom, X is one selected from the group (A) above.

The pyrimidine compound wherein $R^1$ is a hydrogen atom, $R^2$ is 1-methyl-2-propynyloxy, $R^3$ is a fluorine atom, X is one selected from the group (A) above.

The pyrimidine compound wherein $R^1$ is a hydrogen atom, $R^2$ is 1-methyl-2-butynyloxy, $R^3$ is a hydrogen atom, X is one selected from the group (A) above.

The pyrimidine compound wherein $R^1$ is a hydrogen atom, $R^2$ is 1-methyl-2-butynyloxy, $R^3$ is a fluorine atom, X is one selected from the group (A) above.

The pyrimidine compound wherein $R^1$ is a hydrogen atom, $R^2$ is 1-methyl-2-butynyloxy, $R^3$ is a chlorine atom, X is one selected from the group (B) above.

The pests against which the present compounds have an effect may include arthropods (e.g., insects, acarines) and the like, specific examples of which are as follows:

Hemiptera:
Delphacidae such as *Laodelphax striatellus, Nilaparvata lugens, Sogatella furcifera* and the like,
Deltocephalidae such as *Nephotettix cincticeps, Nephotettix virescens* and the like,
Aphididae such as *Aphis gossypii, Myzus persicae* and the like,
Pentatomidae such as *Nezara antennata, Riptortus clavetus* and the like,
Aleyrodidae such as *Trialeurodes vaporariorum, Bemisia argentifolii* and the like,
Coccidae such as *Aonidiella aurantii, Comstockaspis perniciosa, Unaspis citri, Ceroplastes rubens, Icerya purchasi* and the like,
Tingidae,
Psyllidae, and the like;

Lepidoptera:
Pyralidae such as *Chilo suppressalis, Cnaphalocrocis medinalis, Notarcha derogata, Plodia interpunctella* and the like,
Noctuidae such as *Spodoptera litura, Pseudaletia separata, Thoricoplusia* spp., *Heliothis* spp., *Helicoverpa* spp. and the like,
Pieridae such as *Pieris rapae* and the like,
Tortricidae such as *Adoxophyes* spp., *Grapholita molesta, Cydia pomonella* and the like,
Carposimidae such as *Carposina niponensis* and the like,
Lyonetiidae such as *Lyonetia* spp. and the like,
Lymantriidae such as *Lymantria* spp., *Euproctis* spp., and the like,
Yponomeutidae such as *Plutella xylostella* and the like,
Gelechiidae such as *Pectinophora gossypiella* and the like,
Arctiidae such as *Hyphantria cunea* and the like,
Tineidae such as *Tinea translucens, Tineola bisselliella* and the like;

Diptera:
Calicidae such as *Culex pipiens pallens, Culex tritaeniorhynchus, Culex quinquefasciatus* and the like,
*Aedes* spp. such as *Aedes aegypti, Aedes albopictus* and the like,
*Anopheles* such as *Anopheles sinensis* and the like,
Chironomidae,
Muscidae such as *Musca domestica, Muscina stabulans* and the like,
Calliphoridae,
Sarcophagidae,
Fanniidae,
Anthomyiidae such as *Delia platura, Delia antiqua* and the like,
Tephritidae,
Drosophilidae,
Psychodidae,
Tabanidae,
Simuliidae,
Stomoxyidae,
Agromyzidae, and the like;

Coleoptera:
*Diabrotica* spp. such as *Diabrotica virgifera virgifera, Diabrotica undecimpunctata howardi* and the like,
Scarabaeidae such as *Anomala cuprea, Anomala rufocuprea* and the like,
Curculionidae such as *Sitophilus zeamais, Lissorhoptrus oryzophilus, Callosobruchuys chienensis* and the like,
Tenebrionidae such as *Tenebrio molitor, Tribolium castaneum* and the like,
Chrysomelidae such as *Oulema oryzae, Aulacophora femoralis, Phyllotreta striolata, Leptinotarsa decemlineata* and the like,
Anobiidae,
*Epilachna* spp. such as *Epilachna vigintioctopunctata* and the like,
Lyctidae, Bostrychidae,
Cerambycidae,
Paederus fuscipes;
Blattodea:
 *Blattella germanica, Periplaneta fuliginosa, Periplaneta americana, Periplaneta brunnea, Blatta orientalis* and the like;
Thysanoptera:
 *Thrips palmi, Thrips tabaci, Frankliniella occidentalis* and the like;
Hymenoptera:
 Formicidae such as *Monomorium pharaonis*, Vespidae, bethylid wasp, Tenthredimidae such as *Athalia japonica*, and the like;
Orthoptera:
 Gryllotalpidae, Acrididae, and the like;
Aphaniptera:
 *Ctenocephalides felis, Ctenocephalides canis, Pulex irritans, Xenopsylla cheopis*, and the like;
Anoplura:
 *Pediculus humanus corporis, Phthirus pubis, Haematopinus eurysternus, Dalmalinia ovis*, and the like;
Isoptera:
 *Reticulitermes speratus, Coptotermes formosanus*, and the like;
Acarina:
 Tetranychidae such as *Tetranychus urticae, Panonychus citri, Oligonychus* spp., and the like,
 Eriophyidae such as *Aculops pelekassi* and the like,
 Tarsonemidae such as *Polyphagotarsonemus latus*, and the like,
 Tenuipalpidae,
 Tuckerellidae,
 Ixodidae such as *Haemaphysalis longicornis, Haemaphysalis flava, Dermacentor taiwanicus, Ixodes ovatus, Ixodes persulcatus, Boophilus microplus, Rhipicephalus sanguineus*, and the like,
 Acaridae such as *Tyrophagus putrescentiae*, and the like,
 Epidermoptidae such as *Dermatophagoides farinae, Dermatophagoides ptrenyssnus*, and the like,
 Cheyletidae such as *Cheyletus eruditus, Cheyletus malaccensis, Cheyletus moorei*, and the like,
 Dermanyssidae, and the like.

The pests controlling composition of the present invention contains the present compound and an inert carrier. Generally, it is a formulation obtained by mixing the present compound and a carrier such as a solid carrier, a liquid carrier, a gaseous carrier and/or bait for poison bait, and if necessary, adding a surfactant and other adjuvant for formulation. The formulation includes, for example, an oil solution, an emulsion, a flowable formulation, a wettable powder, a granule, a powder, a microcapsule, and the like. These formulations can be converted to use into a poison bait, a sheet. In the pests controlling composition of the present invention, the present compound is usually contained in an amount of 0.01% to 95% by weight.

As the solid carrier used in formulation, there are listed, for example, fine powders or granules of clays (kaolin clay, diatomaceous earth, synthetic water-containing silicon oxide, bentonite, Fubasami clay, acid clay and the like), talcs, ceramics, other inorganic minerals (sericite, quartz, sulfur, activated carbon, calcium carbonate, hydrated silica and the like), chemical fertilizers (ammonia sulfate, ammonia phosphate, ammonia nitrate, urea, ammonia chloride) and the like, and as the liquid carrier, there are listed, for example, water, alcohols (methanol, ethanol and the like), ketones (acetone, methyl ethyl ketone and the like), aromatic hydrocarbons (benzene, toluene, xylene, ethylbenzene, methylnaphthalene and the like), aliphatic hydrocarbons (hexane, cyclohexane, kerosene, light oil and the like), esters (ethyl acetate, butyl acetate and the like), nitrites (acetonitrile, isobutylonitrile and the like), ethers (diisopropyl ether, 1,4-dioxane and the like), acid amides (N,N-dimethylformamide, N,N-dimethylacetamide and the like), halogenated hydrocarbons (dichloromethane, trichloroethane, carbon tetrachloride and the like), dimethyl sulfoxide and vegetable oils (soy bean oil, cotton seed oil and the like).

As the gaseous carrier, there are listed, for example, fluorocarbon, butane gas, LPG (liquefied petroleum gas), dimethyl ether and carbon dioxide.

As the surfactant, there are listed, for example, alkylsulfate salts, alkylsulfonate salts, alkyl aryl sulfonic acid salts, alkyl aryl ethers and their polyoxyethylenated substances, polyethylene glycol ethers, polyhydric alcohol esters, and sugar alcohol derivatives.

As the other formulation auxiliaries, there are listed, for example, fixing agents, dispersing agents, stabilizer and the like, specifically, casein, gelatin, polysaccharides (starch powder, gum Arabic, cellulose derivatives, alginic acid and the like), lignin derivatives, bentonite, saccharides, synthetic water-soluble polymers (polyvinyl alcohol, polyvinylpyrrolidone, polyacrylic acids and the like), PAP (acidic isopropyl phosphate), BHT (2,6-di-tert-butyl-4-methylphenol), BHA (mixture of 2-tert-butyl-4-methoxyphenol and 3-tert-butyl-4-methoxyphenol), vegetable oils, mineral oils, fatty acids and fatty esters.

As the poison bait base material, there are listed, for example, bait components such as crop powders, vegetable oils, saccharides, crystalline cellulose and the like. To the poison bait, antioxidants such as dibutylhydroxytoluene, nordihydroguaiaretic acid and the like, preservatives such as dehydroacetic acid and the like, accidental ingestion-preventing agents for child and pets such as a capsicum powder and the like, harmful insect-attracting aromatics such as cheese aromatics, onion aromatics, peanut oil, and the like, are added, if necessary.

The pests controlling composition of the present invention is applied to pests directly and/or habitats of pests (nest, plant body, soil and the like). When pests parasitic on cultivated plants are controlled, for example, the pests controlling composition of the present invention is sprayed on the ground part of the cultivated plants, the pests controlling composition of the present invention is irrigated near to the stub, and the like.

When the pests controlling composition of the present invention is used to control pests in the agriculture and forestry field, its application amount is usually from 0.1 to 10,000 g in terms of the amount of the present compound per 1000 $m^2$. When the pests controlling composition of the present invention is the formulation of an emulsion, flowable, wettable powders, microcapsule or the like, it is applied after dilution with water to have a concentration of the present compound of usually 10 to 10,000 ppm. When the pests controlling composition of the present invention is the formulation of an oil solution, granule, powder and the like, it is usually applied as it is.

When the pests controlling composition of the present invention is used to control pests in indoor field, the amount of the present compound per $m^2$ of the application area, if treating plane, is usually from 0.001 to 100 mg, and the amount of the present compound per $m^3$ of the application space, if treating space, is usually from 0.001 to 10 mg. When the pests controlling composition of the present invention is the formulation of the an emulsion, flowable, wettable powder, microcapsule and the like, it is applied after dilution with water to have a concentration of the present compound of usually from 0.01 to 100,000 ppm in application thereof. When the pests controlling composition of the present invention is the formulation of an oil solution, aerosol, smoking agent, poison bait and the like, it is usually applied as it is.

The pests controlling composition of the present invention can be used to treat stems and leaves of plants such as crops and the like to be protected from pests, and can also be used to treat beds before planting of nursery plants and the planting hole and stub in planting. Further, for the purpose of controlling pests living in soil of cultivation ground, it may also be used to treat the soil. It is also possible that a resin formulation processed into sheet, string and the like is wound on crops, put around crops and/or placed on the surface of the soil at the stub, and the like.

The pests controlling composition of the present invention can be used together with other insecticides, nematicides, acaricides, bactericides, phytocides, plant growth controlling compositions, synergists, fertilizers, soil improving agents, animal fodders and the like.

Mentioned as such insecticides, acaricides and nematicides are, for example;
organic phosphorus compounds such as fenitrothion, fenthion, pyridaphenthion, diazinon, chlorpyrifos, chlorpyrifos-methyl, acephate, methidathion, disulfoton, DDVP, sulprofos, profenofos, cyanophos, dioxabenzofos, dimethoate, phenthoate, malathion, trichlorfon, azinphosmethyl, monocrotophos, dicrotophos, ethion, fosthiazate and the like; carbamate compounds such as BPMC, benfuracarb, propoxur, carbosulfan, carbaryl, methomyl, ethiofencarb, aldicarb, oxamyl, fenothiocarb, thiodicarb, alanycarb and the like; pyrethroid compounds such as etofenprox, fenvalerate, esfenvalerate, fenpropathrin, cypermethrin, α-cypermethrin, Z-cypermethrin, permethrin, cyhalothrin, λ-cyhalothrin, cyfluthrin, β-cyfluthrin, deltamethrin, cycloprothrin, τ-fluvalinate, flucythrinate, bifenthrin, acrinathrin, tralomethrin, silafluofen, halfenprox and the like; neonicotinoid compounds such as thiamethoxam, dinotefuran, acetamiprid, clothianidin and the like; benzoylphenylurea compounds such as chlorfluazuron, teflubenzuron, flufenoxuron, lufenuron and the like; benzoylhydrazide compounds such as tebufenozide, halofenozide, methoxyfenozide, chromafenozide and the like; thiadiazine derivatives such as buprofezin and the like; nelicetoxin derivatives such as cartap, thiocyclam, bensultap and the like; chlorinated hydrocarbon compounds such as endosulfan, γ-BHC, 1,1-bis(chlorophenyl)-2,2,2-trichloroethanol and the like; formamidine derivatives such as amitraz, chlordimeform and the like; thiourea derivatives such as diafenthiuron and the like; phenylpyrazole compounds such as ethiprole, acetoprole and the like; chlorfenapyr pymetrozine, spinosad, indoxacarb, pyridalyl, pyriproxyfen, fenoxycarb, diofenolan, cyromazine, bromopropylate, tetradifon, quinomethionate, propargite, fenbutatin oxide, hexythiazox, etoxazole, clofentezine, pyridaben, fenpyroximate, tebufenpyrad, pyrimidifen, fenazaquin, acequinocyl, bifenazate, fluacrypyrim, spirodiclofen, spiromesifen, milbemectin, avermectin, emamectin benzoate, azadirachtin, polynactin complex [tetranactin, dinactin, trinactin] and the like.

The present invention will be illustrated further in detail by the following formulation examples, test examples and the like, but the present invention is not limited to these examples.

In production examples and reference production examples, regarding ¹H-NMR, data measured using tetramethylsilane as an internal standard in a deuterochloroform solvent are shown in terms of chemical shift ([ppm] value) unless otherwise stated.

WORKING EXAMPLES

Production Example 1

Into 3 ml of ethanol was resolved 0.3 g of 4-(2-butynyloxy)-6-chloro-5-fluoropyrimidine, 0.45 g of 2-methylpyperidine was added therein, and the mixture was stirred for 5 hours under reflux condition. The reaction mixture was cooled to near room temperature and concentrated. The residue was subjected to silica gel column chromatography to obtain 0.28 g of 4-(2-butynyloxy)-5-fluoro-6-(2-methylpiperidino)pyrimidine (hereinafter, referred to as Compound (1)).

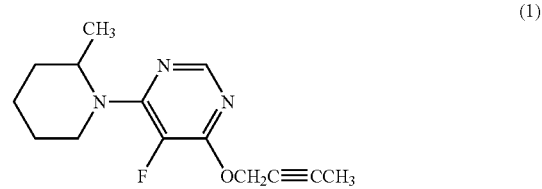

¹H-NMR: 1.25 (d, 3H), 1.58-1.79 (m, 6H), 1.88 (t, 3H), 3.14-3.18 (m, 1H), 4.21-4.24 (m, 1H), 4.65-4.78 (m, 1H), 4.97 (q, 2H), 8.04 (s, 1H)

Production Example 2

Into 3 ml of ethanol was resolved 0.3 g of 4-(2-butynyloxy)-6-chloro-5-fluoropyrimidine, 0.38 g of piperidine was added therein, and the mixture was stirred for 7 hours under reflux condition. The reaction mixture was cooled to near room temperature and concentrated. The residue was subjected to silica gel column chromatography to obtain 0.37 g of 4-(2-butynyloxy)-5-fluoro-6-piperidinopyrimidine (hereinafter, referred to as Compound (2)).

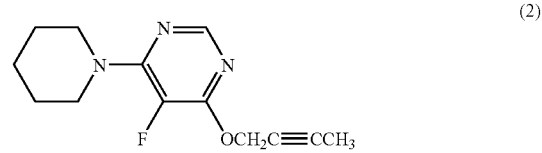

¹H-NMR: 1.60-1.72 (m, 6H), 1.87 (t, 3H), 3.63-3.69 (m, 4H), 4.97 (q, 2H), 8.04 (s, 1H)

Production Example 3

Into 3 ml of ethanol was resolved 0.3 g of 4-(2-butynyloxy)-6-chloro-5-fluoropyrimidine, 0.45 g of 3-methylpiperidine was added therein, and the mixture was stirred for 10 hours under reflux condition. The reaction mixture was cooled to near room temperature, and concentrated. Into the residue was added a saturated ammonium chloride aqueous solution, and the mixture was extracted with tert-butyl methyl ether three times. The organic layers were washed with a saturated sodium chloride aqueous solution, dried over anhydrous magnesium sulfate and concentrated. The residue was subjected to silica gel column chromatography to obtain 0.37 g of 4-(2-butynyloxy)-5-fluoro-6-(3-methylpiperidino) pyrimidine (hereinafter, referred to as Compound (3)).

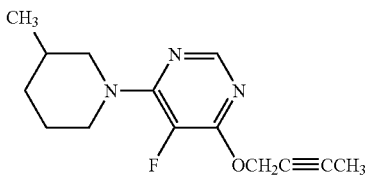

(3)

¹H-NMR: 0.92 (d, 3H), 1.17-1.23 (m, 1H), 1.52-1.77 (m, 3H), 1.81-1.91 (m, 4H, involving a triplet at 1.87), 2.60-2.64 (m, 1H), 2.92-3.01 (m, 1H), 4.26-4.38 (m, 2H), 4.97 (q, 2H), 8.04 (s, 1H)

Production Example 4

Into 3 ml of ethanol was resolved 0.3 g of 4-(2-butynyloxy)-6-chloro-5-fluoropyrimidine, 0.51 g of 3,5-dimethylpiperidine (cis/trans=about 3/1) was added therein, and the mixture was stirred for 8 hours under reflux condition. The reaction mixture was cooled to near room temperature, and concentrated. Into the residue was added a saturated ammonium chloride aqueous solution, and the mixture was extracted with tert-butyl methyl ether three times. The organic layers were washed with a saturated sodium chloride aqueous solution, dried over anhydrous magnesium sulfate and concentrated. The residue was subjected to silica gel column chromatography to obtain 0.40 g of 4-(2-butynyloxy)-5-fluoro-6-(3,5-dimethylpiperidino)pyrimidine (hereinafter, referred to as Compound (4)). Compound (4) had the cis/trans diastereomer originated two methyls on the piperidine ring. The ratio of the cis/trans diastereomer was about 3.3/1.

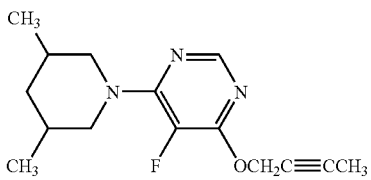

(4)

¹H-NMR: 0.80 (dd, 1H), 0.91 (d, 6H), 1.60-1.72 (m, 2H), 1.81-1.89 (m, 4H, involving a triplet at 1.87), 2.40 (dd, 2H), 4.39 (dd, 2H), 4.97 (q, 2H), 8.03 (s, 1H); 0.94 (s), 1.49 (t), 1.94-2.03 (m), 3.31 (dd), 3.75 (dd), 8.01 (s)

Production Example 5

Into 3 ml of ethanol was resolved 0.3 g of 4-(2-butynyloxy)-6-chloro-5-fluoropyrimidine, 0.45 g of hexamethyleneimine was added therein, and the mixture was stirred for 10 hours under reflux condition. The reaction mixture was cooled to near room temperature, and concentrated. The residue was subjected to silica gel column chromatography to obtain 0.29 g of 1-{6-(2-butynyloxy)-5-fluoro-4-pyrimidinyl}hexahydro-1H-azepine (hereinafter, referred to as Compound (5)).

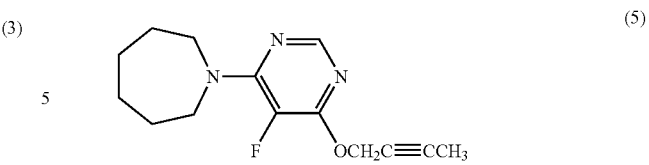

(5)

¹H-NMR: 1.56-1.60 (m, 4H), 1.77-1.81 (m, 4H), 1.87 (t, 3H), 3.74-3.77 (m, 4H), 4.97 (q, 2H), 8.01 (s, 1H)

Production Example 6

0.2 g of 4-(2-butynyloxy)-6-chloro-5-fluoropyrimidine and 0.30 g of 2,5-dimethylpyrrolidine were mixed and left for 18 hours at room temperature. Into the reaction mixture was added a saturated ammonium chloride aqueous solution, and the mixture was extracted with tert-butyl methyl ether three times. The organic layers were washed with a saturated sodium chloride aqueous solution, dried over anhydrous magnesium sulfate and concentrated. The residue was subjected to silica gel column chromatography to obtain 0.25 g of 4-(2-butynyloxy)-5-fluoro-6-(2,5-dimethyl-1-pyrrolidinyl)pyrimidine (hereinafter, referred to as Compound (6)).

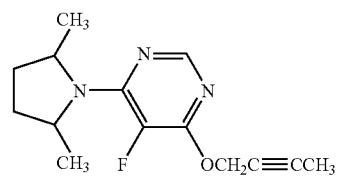

(6)

¹H-NMR: 1.33 (d, 6H), 1.70-1.76 (m, 2H), 1.87 (t, 3H), 2.01-2.07 (m, 2H), 4.26-4.34 (m, 2H), 4.97 (q, 2H), 8.03 (s, 1H)

Production Example 7

Into 3 ml of ethanol was resolved 0.3 g of 4-(2-butynyloxy)-6-chloropyrimidine, 0.56 g of 3,5-dimethylpiperidine (cis/trans=about 3/1) was added therein, and the mixture was stirred for 10 hours under reflux condition. The reaction mixture was cooled to near room temperature, and concentrated. Into the residue was added a saturated ammonium chloride aqueous solution, and the mixture was extracted with tert-butyl methyl ether three times. The organic layers were washed with a saturated sodium chloride aqueous solution, dried over anhydrous magnesium sulfate and concentrated. The residue was subjected to silica gel column chromatography to obtain 0.44 g of 4-(2-butynyloxy)-6-(3,5-dimethylpiperidino)pyrimidine (hereinafter, referred to as Compound (7)). Compound (7) had the cis/trans diastereomer originated two methyls on the piperidine ring. The ratio of the cis/trans diastereomer was about 3.1/1.

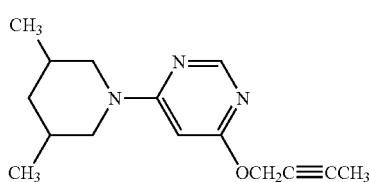

(7)

¹H-NMR: 0.81 (dd, 1H), 0.92 (d, 6H), 1.55-1.68 (m, 2H), 1.80-1.89 (m, 4H, involving a triplet at 1.86), 2.31 (dd, 2H), 4.23 (dd, 2H), 4.91 (q, 2H), 5.87 (s, 1H), 8.29 (s, 1H); 1.49 (t), 1.89-1.99 (m), 3.18 (dd), 3.64 (dd), 5.85 (s), 8.27 (s)

Production Example 8

Into 3 ml of ethanol was resolved 0.3 g of 4-(2-butynyloxy)-5,6-dichloropyrimidine, 0.47 g of 3,5-dimethylpiperidine (cis/trans=about 3/1) was added therein, and the mixture was stirred for 8 hours under reflux condition. The reaction mixture was cooled to near room temperature, and concentrated. Into the residue was added a saturated ammonium chloride aqueous solution, and the mixture was extracted with tert-butyl methyl ether three times. The organic layers were washed with a saturated sodium chloride aqueous solution, dried over anhydrous magnesium sulfate and concentrated. The residue was subjected to silica gel column chromatography to obtain 0.36 g of 4-(2-butynyloxy)-5-chloro-6-(3,5-dimethylpiperidino)pyrimidine (hereinafter, referred to as Compound (8)). Compound (8) had the cis/trans diastereomer originated two methyls on the piperidine ring. The ratio of the cis/trans diastereomer was about 3.6/1.

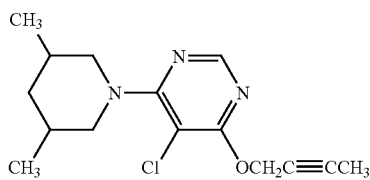

(8)

¹H-NMR: 0.77 (dd, 1H), 0.91 (d, 6H), 1.70-1.91 (m, 6H, involving a triplet at 1.86), 2.38 (dd, 2H), 4.24 (dd, 2H), 4.99 (q, 2H), 8.22 (s, 1H); 0.97 (d), 1.45-1.48 (m), 2.05-2.09 (m), 3.28 (dd), 3.59 (dd)

Production Example 9

Into 3 ml of ethanol was resolved 0.3 g of 4-(2-butynyloxy)-6-chloro-5-methylpyrimidine, 0.47 g of 3,5-dimethylpiperidine (cis/trans=about 3/1) was added therein, and the mixture was stirred for 16 hours under reflux condition. The reaction mixture was cooled to near room temperature, and concentrated. Into the residue was added a saturated ammonium chloride aqueous solution, and the mixture was extracted with tert-butyl methyl ether three times. The organic layers were washed with a saturated sodium chloride aqueous solution, dried over anhydrous magnesium sulfate and concentrated. The residue was subjected to silica gel column chromatography to obtain 0.33 g of 4-(2-butynyloxy)-5-methyl-6-(3,5-dimethylpiperidino)pyrimidine (hereinafter, referred to as Compound (9)). Compound (9) had the cis/trans diastereomer originated two methyls on the piperidine ring. The ratio of the cis/trans diastereomer was about 3.8/1.

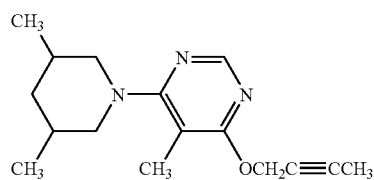

(9)

¹H-NMR: 0.75 (dd, 1H), 0.91 (d, 6H), 1.71-1.89 (m, 6H, involving a triplet at 1.87), 2.06 (s, 3H), 2.34 (dd, 2H), 3.67 (dd, 2H), 4.95 (q, 2H), 8.33 (s, 1H); 1.01 (d), 1.43-1.47 (m), 2.09 (s), 2.94 (dd), 3.29 (dd)

Production Example 10

0.2 g of 4-chloro-5-fluoro-6-(2-pentynyloxy)pyrimidine and 0.29 g of 3-methylpiperidine were mixed and left for 3 hours at room temperature. The reaction mixture was subjected to silica gel column chromatography to obtain 0.23 g of 5-fluoro-4-(3-methylpiperidino)-6-(2-pentynyloxy)pyrimidine (hereinafter, referred to as Compound (10)).

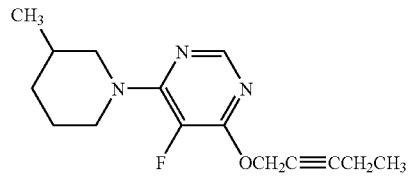

(10)

¹H-NMR: 0.92 (d, 3H), 1.12-1.23 (m, 4H, involving a triplet at 1.14), 1.52-1.77 (m, 3H), 1.82-1.89 (m, 1H), 2.24 (qt, 2H), 2.62 (dd, 1H), 2.95 (dd, 1H), 4.26-4.34 (m, 2H), 4.99 (t, 2H), 8.03 (s, 1H)

Production Example 11

0.2 g of 4-chloro-5-fluoro-6-(2-pentynyloxy)pyrimidine and 0.32 g of 3,5-dimethylpiperidine (cis/trans=about 3/1) were mixed and left for 3 hours at room temperature. The reaction mixture was subjected to silica gel column chromatography to obtain 0.23 g of 4-(3,5-dimethylpiperidino)-5-fluoro-6-(2-pentynyloxy)pyrimidine (hereinafter, referred to as Compound (11)). Compound (11) had the cis/trans diastereomer originated two methyls on the piperidine ring. The ratio of the cis/trans diastereomer was about 3.8/1.

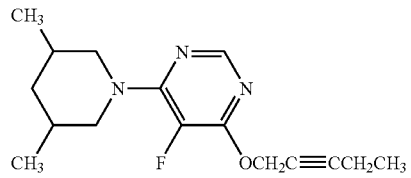

(11)

¹H-NMR: 0.80 (dd, 1H), 0.91 (d, 6H), 1.14 (t, 3H), 1.63-1.75 (m, 2H), 1.80-1.88 (m, 1H), 2.24 (qt, 2H), 2.40 (dd, 2H), 4.39 (dd, 2H), 4.99 (t, 2H), 8.03 (s, 1H); 0.94 (d), 1.46-1.49 (m), 1.93-2.02 (m), 3.31 (dd), 3.75 (dd), 8.01 (s)

Production Example 12

0.2 g of 4-chloro-5-fluoro-6-(2-pentynyloxy)pyrimidine and 0.24 g of piperidine were mixed and left for 3 hours at room temperature. The reaction mixture was subjected to silica gel column chromatography to obtain 0.24 g of 5-fluoro-4-piperidino-6-(2-pentynyloxy)pyrimidine (hereinafter, referred to as Compound (12)).

¹H-NMR: 1.14 (t, 3H), 1.60-1.71 (m, 6H), 2.24 (qt, 2H), 3.67-3.71 (m, 4H), 4.99 (t, 2H), 8.03 (s, 1H)

Production Example 13

0.2 g of 4-chloro-5-fluoro-6-(2-pentynyloxy)pyrimidine and 0.2 g of 2,5-dimethylpyrroridine were mixed and left for 13 hours at room temperature. The reaction mixture was subjected to silica gel column chromatography to obtain 0.12 g of 4-(2,5-dimethyl-1-pyrrolidinyl)-5-fluoro-6-(2-pentynyloxy)pyrimidine (hereinafter, referred to as Compound (13)).

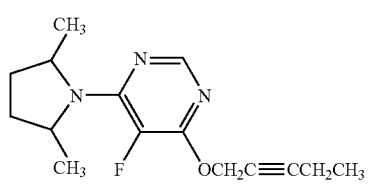

¹H-NMR: 1.15 (t, 3H), 1.33 (d, 6H), 1.69-1.78 (m, 2H), 2.00-2.09 (m, 2H), 2.24 (qt, 2H), 4.24-4.33 (m, 2H), 4.99 (t, 2H), 8.03 (s, 1H)

Production Example 14

0.2 g of 4-chloro-5-fluoro-6-(2-pentynyloxy)pyrimidine and 0.28 g of hexamethyleneimine were mixed and left for 3 hours at room temperature. The reaction mixture was subjected to silica gel column chromatography to obtain 0.26 g of 1-{5-fluoro-6-(2-pentynyloxy)-4-pyrimidinyl}hexahydro-1H-azepine (hereinafter, referred to as Compound (14)).

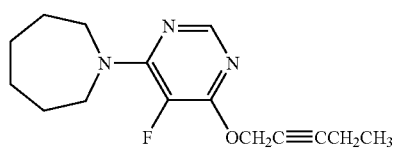

¹H-NMR: 1.15 (t, 3H), 1.52-1.61 (m, 4H), 1.72-1.79 (m, 4H), 2.24 (qt, 2H), 3.65-3.74 (m, 4H), 4.99 (t, 2H), 8.01 (s, 1H)

Production Example 15

0.07 g of sodium hydride (60% oil suspension) was suspended in 2 ml of tetrahydrofuran. 0.5 ml of tetrahydrofuran solution of 0.13 g of 2-pentyn-1-ol was added dropwise at 0° C. therein, and the mixture was stirred for 10 minutes. Into the mixture was added dropwise 0.5 ml of tetrahydrofuran solution of 0.3 g of 4-chloro-6-(3,5-dimethylpiperidino)pyrimidine obtained the Reference Production Example 6, and stirred for 6 hours at room temperature. Into the reaction mixture was added a saturated ammonium chloride aqueous solution, and the mixture was extracted with tert-butyl methyl ether three times. The organic layers were washed with a saturated sodium chloride aqueous solution, dried over anhydrous magnesium sulfate and concentrated. The residue was subjected to silica gel column chromatography to obtain 0.15 g of 4-(3,5-dimethylpiperidino)-6-(2-pentynyloxy)pyrimidine (hereinafter, referred to as Compound (15)). Compound (15) had the cis/trans diastereomer originated two methyls on the pyperidine ring. The ratio of the cis/trans diastereomer was about 8.2/1.

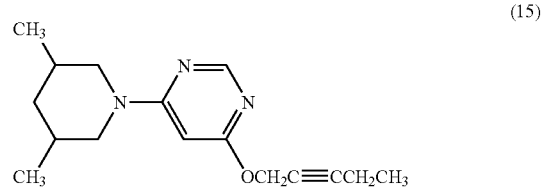

¹H-NMR: 0.81 (dd, 1H), 0.92 (d, 6H), 1.15 (t, 3H), 1.55-1.72 (m, 2H), 1.80-1.87 (m, 1H), 2.20-2.36 (m, 4H), 4.23-4.26 (m, 2H), 4.93 (t, 2H), 5.88 (s, 1H), 8.29 (s, 1H); 1.89-2.00 (m), 3.18 (dd), 3.64 (dd), 5.86 (s), 8.27 (s)

Production Example 16

Into 2 ml of N,N-dimethylformamide was resolved 183 mg of 4-chloro-6-(2-butynyloxy)pyrimidine, 166 mg of potassium carbonate and 85 mg of piperidine was added therein, and the mixture was stirred for 5 hours at 80° C. The reaction mixture was cooled to near room temperature, ethyl acetate was added therein, and the mixture was washed with a saturated sodium chloride aqueous solution three times. The organic layers were dried over anhydrous magnesium sulfate and concentrated. The residue was subjected to silica gel column chromatography to obtain 178 mg of 4-(2-butynyloxy)-6-piperidinopyrimidine (hereinafter, referred to as Compound (16)).

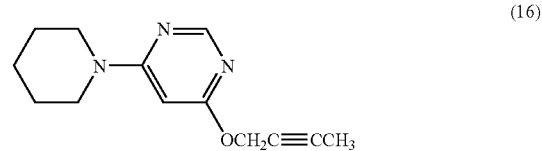

¹H-NMR: 1.5-1.8 (m, 6H), 1.87 (t, 3H), 3.55 (t, 4H), 4.91 (q, 2H), 5.86 (s, 1H), 8.30 (s, 1H)

Production Example 17

Into 2 ml of N,N-dimethylformamide was resolved 183 mg of 4-chloro-6-(2-butynyloxy)pyrimidine, 166 mg of potassium carbonate and 71 mg of pyrrolidine was added therein, and the mixture was stirred for 4 hours at 55-60° C. The reaction mixture was cooled to near room temperature, ethyl acetate was added therein, and the mixture was washed with a saturated sodium chloride aqueous solution three times. The organic layers were dried over anhydrous magnesium sulfate and concentrated. The residue was subjected to silica gel column chromatography to obtain 170 mg of 4-(2-butyny-loxy)-6-(1-pyrrolidinyl)pyrimidine (hereinafter, referred to as Compound (17)).

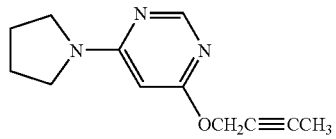

(17)

¹H-NMR: 1.87 (t, 3H), 2.00 (brs, 4H), 3.45 (brs, 4H), 4.92 (q, 2H), 5.65 (s, 1H), 8.30 (s, 1H)

Production Example 18

Into 2 ml of N,N-dimethylformamide was resolved 183 mg of 4-chloro-6-(2-butynyloxy)pyrimidine, 166 mg of potassium carbonate and 99 mg of 4-methylpiperidine was added therein, and the mixture was stirred for 4 hours at 80° C. The reaction mixture was cooled to near room temperature, ethyl acetate was added therein, and the mixture was washed with a saturated sodium chloride aqueous solution three times. The organic layers were dried over anhydrous magnesium sulfate and concentrated. The residue was subjected to silica gel column chromatography to obtain 206 mg of 4-(2-butyny-loxy)-6-(4-methylpiperidino) pyrimidine (hereinafter, referred to as Compound (18)).

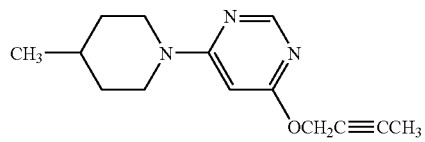

(18)

¹H-NMR: 0.96 (d, 3H), 1.0-1.3 (m, 2H), 1.5-1.8 (m, 3H), 1.87 (t, 3H), 2.85 (dt, 2H), 4.2-4.35 (m, 2H), 4.91 (q, 2H), 5.87 (s, 1H), 8.30 (s, 1H)

Production Example 19

Into 2 ml of N,N-dimethylformamide was resolved 183 mg of 4-chloro-6-(2-butynyloxy)pyrimidine, 166 mg of potassium carbonate and 99 mg of 3-methylpiperidine was added therein, and the mixture was stirred for 4 hours at 80° C. The reaction mixture was cooled to near room temperature, ethyl acetate was added therein, and the mixture was washed with a saturated sodium chloride aqueous solution three times. The organic layers were dried over anhydrous magnesium sulfate and concentrated. The residue was subjected to silica gel column chromatography to obtain 181 mg of 4-(2-butyny-loxy)-6-(3-methylpiperidino) pyrimidine (hereinafter, referred to as Compound (19)).

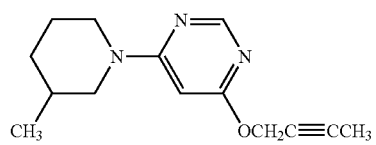

(19)

¹H-NMR: 0.93 (d, 3H), 1.05-1.3 (m, 1H), 1.4-1.85 (m, 4H), 1.87 (t, 3H), 2.45-2.6 (m, 1H), 2.85 (dt, 1H), 4.1-4.25 (m, 2H), 4.91 (q, 2H), 5.87 (s, 1H), 8.30 (s, 1H)

Production Example 20

Into 2 ml of N,N-dimethylformamide was resolved 183 mg of 4-chloro-6-(2-butynyloxy)pyrimidine, 166 mg of potassium carbonate and 99 mg of 2-methylpiperidine was added therein, and the mixture was stirred for 4 hours at 80° C. and 3 hours at 120° C. The reaction mixture was cooled to near room temperature, ethyl acetate was added therein, and the mixture was washed with a saturated sodium chloride aqueous solution three times. The organic layers were dried over anhydrous magnesium sulfate and concentrated. The residue was subjected to silica gel column chromatography to obtain 66 mg of 4-(2-butynyloxy)-6-(2-methylpiperidino)pyrimidine (hereinafter, referred to as Compound (20)).

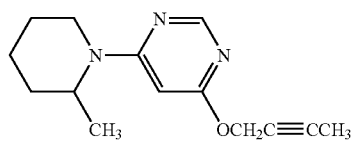

(20)

¹H-NMR: 1.16 (d, 3H), 1.4-1.6 (m, 1H), 1.6-1.8 (m, 5H), 1.87 (t, 3H), 2.91 (dt, 1H), 4.1-4.2 (m, 1H), 4.5-4.6 (m, 1H), 4.91 (q, 2H), 5.84 (s, 1H), 8.30 (s, 1H)

Production Example 21

Into 2 ml of N,N-dimethylformamide was resolved 183 mg of 4-chloro-6-(2-butynyloxy)pyrimidine, 166 mg of potassium carbonate and 85 mg of 2-methylpyrrolidine was added therein, and the mixture was stirred for 7 hours at 60° C. The reaction mixture was cooled to near room temperature, ethyl acetate was added therein, and the mixture was washed with a saturated sodium chloride aqueous solution three times. The organic layers were dried over anhydrous magnesium sulfate and concentrated. The residue was subjected to silica gel column chromatography to obtain 207 mg of 4-(2-butyny-loxy)-6-(2-methyl-pyrrolidin-1-yl)pyrimidine (hereinafter, referred to as Compound (21)).

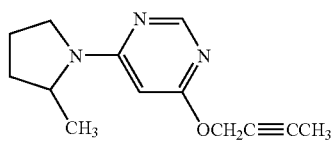

(21)

¹H-NMR: 1.21 (d, 3H), 1.6-1.8 (m, 1H), 1.88 (t, 3H), 1.9-2.1 (m, 3H), 3.2-3.4 (m, 1H), 3.4-3.6 (m, 1H), 4.0-4.2 (m, 1H), 4.92 (q, 2H), 5.66 (s, 1H), 8.31 (s, 1H)

Production Example 22

0.3 g of 4-chloro-6-(2-butynyloxy)pyrimidine and 0.56 g of 2-ethylpiperidine were mixed and left for 18 hours at 80° C. The reaction mixture was cooled to near room temperature and subjected to silica gel column chromatography to obtain 0.14 g of 4-(2-butynyloxy)-6-(2-ethylpiperidino)pyrimidine (hereinafter, referred to as Compound (22)).

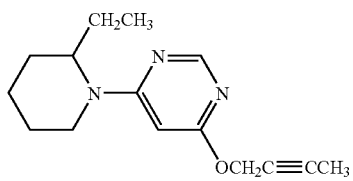

(22)

¹H-NMR: 0.86 (t, 3H), 1.41-1.78 (m, 8H), 1.87 (t, 3H), 2.89 (td, 2H), 4.14-3.38 (m, 2H), 4.91 (q, 2H), 5.83 (s, 1H), 8.28 (s, 1H)

Production Example 23

Into 3 ml of N,N-dimethylformamide was resolved 0.3 g of 4-chloro-6-(2-butynyloxy)pyrimidine, 0.57 g of potassium carbonate and 0.25 g of cis-3,5-dimethylpiperidine hydrochloride was added therein, and the mixture was stirred for 40 minutes at 70° C. The reaction mixture was cooled to near room temperature, a saturated ammonium chloride aqueous solution was added therein, and the mixture was extracted with tert-buthyl methyl ether three times. The organic layers were washed with a saturated sodium chloride aqueous solution three times. The organic layers were dried over anhydrous magnesium sulfate and concentrated. The residue was subjected to silica gel column chromatography to obtain 0.41 g of 4-(2-butynyloxy)-6-(cis-3,5-dimethylpiperidino)pyrimidine (hereinafter, referred to as Compound (23)).

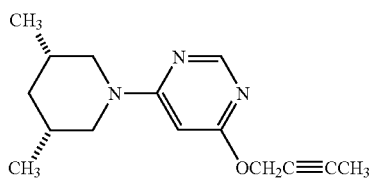

(23)

¹H-NMR: 0.80 (dd, 1H), 0.92 (d, 6H), 1.54-1.67 (m, 2H), 1.79-1.88 (m, 4H, involving a triplet at 1.86), 2.31 (dd, 2H), 4.25 (dd, 2H), 4.91 (q, 2H), 5.87 (s, 1H), 8.30 (s, 1H)

Production Example 24

0.3 g of 4-chloro-6-(2-butynyloxy)pyrimidine and 0.25 g of 3-trifluoromethylpiperidine were mixed and left for 10 hours at room temperature. The reaction mixture was subjected to silica gel column chromatography to obtain 0.30 g of 4-(2-butynyloxy)-6-(3-trifluoromethylpiperidino)pyrimidine (hereinafter, referred to as Compound (24)).

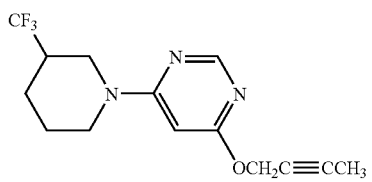

(24)

¹H-NMR: 1.36-1.60 (m, 2H), 1.72-1.83 (m, 4H, involving a triplet at 1.87), 1.95-2.14 (m, 1H), 2.19-2.24 (m, 1H), 2.75-2.84 (m, 2H), 4.13 (brd, 1H), 4.53 (brd, 1H), 4.84 (q, 2H), 5.82 (s, 1H), 8.24 (s, 1H)

Production Example 25

0.2 g of 4-chloro-6-(2-pentynyloxy)pyrimidine and 0.23 g of 3-trifluoromethylpiperidine were mixed and left for 10 hours at room temperature. The reaction mixture was subjected to silica gel column chromatography to obtain 0.15 g of 6-(2-pentynyloxy)-4-(3-trifluoromethylpiperidino)pyrimidine (hereinafter, referred to as Compound (25)).

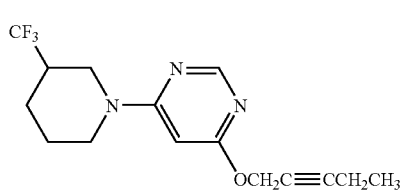

(25)

¹H-NMR: 1.15 (t, 3H), 1.45-1.68 (m, 2H), 1.79-1.88 (m, 1H), 2.04-2.13 (m, 1H), 2.25 (qt, 3H), 2.80-2.93 (m, 2H), 4.22 (brd, 1H), 4.61 (brd, 1H), 4.95 (q, 2H), 5.92 (s, 1H), 8.33 (s, 1H)

Production Example 26

Into 2 ml of N,N-dimethylformamide was resolved 0.2 g of 4-(2-butynyloxy)-5-fluoro-6-chloropyrimidine, 0.28 g of potassium carbonate and 0.15 g of 3-trifluoromethylpiperidine was added therein, and the mixture was stirred for 5 hours at 70° C. The reaction mixture was cooled to near room temperature, ethyl acetate was added therein, and the mixture was washed with a saturated sodium chloride aqueous solution three times. The organic layers were dried over anhydrous magnesium sulfate and concentrated. The residue was subjected to silica gel column chromatography to obtain 0.28 g of 4-(2-butynyloxy)-5-fluoro-6-(3-methylpiperidino)pyrimidine (hereinafter, referred to as Compound (26)).

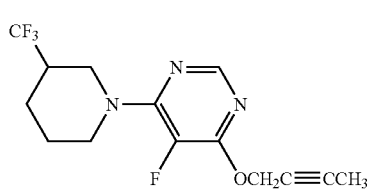

(26)

¹H-NMR: 1.54-1.68 (m, 2H), 1.81-1.90 (m, 4H, involving a triplet at 1.87), 2.05-2.14 (m, 1H), 2.30-2.44 (m, 1H,), 2.92-3.02 (m, 2H), 4.38 (brd, 1H), 4.65 (q, 1H), 4.99 (q, 2H), 8.08 (s, 1H)

Production Example 27

Into 4 ml of N,N-dimethylformamide was resolved 0.37 g of 4-(2-butynyloxy)-6-chloropyrimidine, 0.56 g of potassium carbonate and 0.2 g of 3,3-dimethylpyrrolidine was added therein, and the mixture was stirred for 6 hours at 80° C. The reaction mixture was cooled to near room temperature, ethyl acetate was added therein, and the mixture was washed with a saturated sodium chloride aqueous solution three times. The organic layers were dried over anhydrous magnesium sulfate and concentrated. The residue was subjected to silica gel column chromatography to obtain 0.11 g of 4-(2-butynyloxy)-6-(3,3-dimethylpyrrolidin-1-yl)pyrimidine (hereinafter, referred to as Compound (27)).

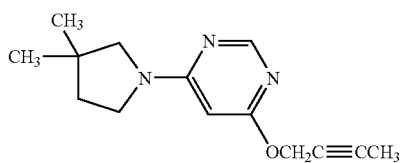

(27)

¹H-NMR: 1.13 (s, 6H), 1.75-1.84 (m, 2H), 1.87 (t, 3H), 2.94-3.75 (br, 4H), 4.92 (q, 2H,), 5.62 (s, 1H), 8.31 (s, 1H)

Production Example 28

Into 4 ml of N,N-dimethylformamide was resolved 0.36 g of 4-(2-butynyloxy)-6-chloro-5-fluoropyrimidine, 0.62 g of potassium carbonate and 0.25 g of 3,3-dimethylpyrrolidine was added therein, and the mixture was stirred for 6 hours at 80° C. The reaction mixture was cooled to near room temperature, ethyl acetate was added therein, and the mixture was washed with a saturated sodium chloride aqueous solution three times. The organic layers were dried over anhydrous magnesium sulfate and concentrated. The residue was subjected to silica gel column chromatography to obtain 0.15 g of 4-(2-butynyloxy)-5-fluoro-6-(3,3-dimethylpyrrolidin-1-yl) pyrimidine (hereinafter, referred to as Compound (28)).

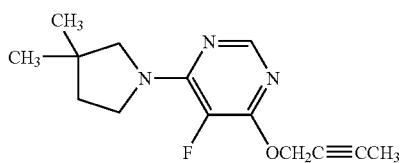

(28)

¹H-NMR: 1.13 (s, 6H), 1.73 (t, 2H), 1.87 (t, 3H), 3.42 (d, 2H), 3.76 (td, 2H), 4.97 (q, 2H,), 8.02 (s, 1H)

Production Example 29

0.10 g of sodium hydride (60% oil suspension) was suspended in 3 ml of tetrahydrofuran. 1 ml of tetrahydrofuran solution of 0.16 g of 2-butyn-1-ol was added dropwise therein, and the mixture was stirred for 10 minutes. Into the mixture was added dropwise 1 ml of tetrahydrofuran solution of 0.31 g of 4-chloro-6-(cis-3,5-dimethylpiperidino)-5-fluoropyrimidine and stirred for 6 hours at 60° C. Into the reaction mixture was added a saturated ammonium chloride aqueous solution, and the mixture was extracted with tert-butyl methyl ether three times. The organic layers were washed with a saturated sodium chloride aqueous solution, dried over anhydrous magnesium sulfate and concentrated. The residue was subjected to silica gel column chromatography to obtain 0.32 g of 4-(2-butynyloxy)-5-fluoro-6-(cis-3,5-dimethylpiperidino)pyrimidine (hereinafter, referred to as Compound (29)).

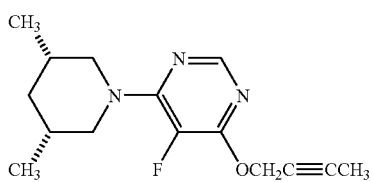

(29)

¹H-NMR: 0.80 (dd, 1H), 0.91 (d, 6H), 1.63-1.76 (m, 2H), 1.81-1.88 (m, 4H, involving a triplet at 1.87), 2.40 (dd, 2H), 4.39 (dd, 2H), 4.97 (q, 2H,), 8.04 (s, 1H)

Production Example 30

0.16 g of sodium hydride (60% oil suspension) was suspended in 4 ml of tetrahydrofuran. 1 ml of tetrahydrofuran solution of 0.27 g of 2-butyn-1-ol was added dropwise therein, and the mixture was stirred for 10 minutes at room temperature. Into the mixture was added dropwise 1 ml of tetrahydrofuran solution of 0.64 g of 4-chloro-6-(3,5-diethylpiperidino)pyrimidine, wherein the ratio of cis/trans diasteromer on the piperidino ring was 1:1, and stirred for 5 hours at 60° C. Into the reaction mixture was added a saturated ammonium chloride aqueous solution, and the mixture was extracted with tert-butyl methyl ether three times. The organic layers were washed with a saturated sodium chloride aqueous solution, dried over anhydrous magnesium sulfate and concentrated. The residue was subjected to silica gel column chromatography to obtain 0.41 g of 4-(2-butynyloxy)-6-(3,5-diethylpiperidino)pyrimidine (hereinafter, referred to as Compound (30)). Compound (30) had the cis/trans diastereomer originated two ethyls on the pyperidine ring. The ratio of the cis/trans diastereomer was about 1/1.

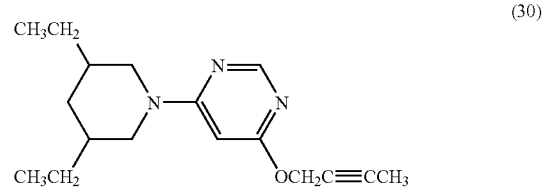

(30)

¹H-NMR: 0.73 (dd, 0.5H), 0.88-0.95 (m, 6H), 1.07 (t, 0.5H), 1.20-1.42 (m, 4H), 1.52-1.64 (m, 2H), 1.80-1.99 (m, 4H), 2.34 (dd, 1H), 3.30 (dd, 1H), 3.62 (dd, 1 h), 4.28-4.37 (m, 1H), 4.90-4.93 (m, 2H), 5.85 (s, 0.5H), 5.87 (s, 0.5H), 8.27 (s, 0.5H), 8.30 (s, 0.5)

Production Example 31

Into 2 ml of acetnitrile were added 0.20 g of 4-(2-butynyloxy)-6-chloropyrimidine, 0.45 g of potassium carbonate and 0.20 g of 3,3-dimethylpiperidine hydrochloride, and the mixture was stirred for 2 hours at 80° C. The reaction mixture was cooled to near room temperature, a saturated ammonium chloride aqueous solution was added therein, and the mixture was extracted with tert-butyl methyl ether three times. The organic layers were washed with a saturated sodium chloride aqueous solution, dried over anhydrous magnesium sulfate and concentrated. The residue was subjected to silica gel column chromatography to obtain 0.27 g of 4-(2-butynyloxy)-6-(3,3-dimethylpiperidino)pyrimidine (hereinafter, referred to as Compound (31)).

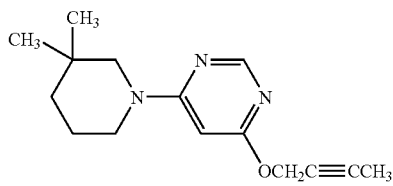

(31)

Production Example 32

0.12 g of sodium hydride (60% oil suspention) was suspended in 2 ml of tetrahydrofuran. 0.18 g of 3,3-dimethylpiperidine hydrochloride and 0.20 g of 4-(2-butynyloxy)-6-chloro-5-fluoropyrimidine were added therein, and the mixture was stirred for 1 hour at 60° C. After the reaction mixture was cooled to near room temperature, a saturated ammonium chloride aqueous solution was added therein, and the mixture was extracted with tert-butyl methyl ether three times. The organic layers were washed with a saturated sodium chloride aqueous solution, dried over anhydrous magnesium sulfate and concentrated. The residue was subjected to silica gel column chromatography to obtain 0.05 g of 4-(2-butynyloxy)-6-(3,3-dimethylpiperidino)-5-fluoropyrimidine (hereinafter, referred to as Compound (32)).

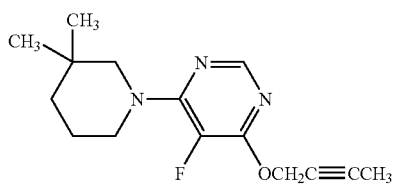

(32)

$^1$H-NMR: 0.93 (s, 6H), 1.43-1.48 (m, 2H), 1.61-1.72 (m, 2H), 1.87 (t, 3H), 3.39 (s, 2H), 3.62-3.67 (m, 2H), 4.97 (q, 2H), 8.02 (s, 1H)

Production Example 33

0.05 g of sodium hydride (60% oil suspention) was suspended in 2 ml of tetrahydrofuran. The 0.5 ml of tetrahydrofuran solution of 0.08 g of 2-butyn-1-ol was added dropwise at room temperature therein, and the mixture was stirred for 10 minutes. Into the mixture was added dropwise 0.5 ml of tetrahydrofuran solution of 0.22 g of 4-chloro-6-(2-ethylpiperidino)pyrimidine at room temperature, and stirred for 6 hours at 60° C. After the reaction mixture was cooled to near room temperature, a saturated ammonium chloride aqueous solution was added therein, and the mixture was extracted with tert-butyl methyl ether three times. The organic layers were washed with a saturated sodium chloride aqueous solution, dried over anhydrous magnesium sulfate and concentrated. The residue was subjected to silica gel column chromatography to obtain 0.23 g of 4-(2-butynyloxy)-6-(2-ethylpiperidino)-5-fluoropyrimidine (hereinafter, referred to as Compound (33)).

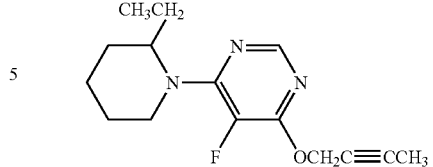

(33)

$^1$H-NMR: 0.87 (t, 3H), 1.48-1.72 (m, 7H), 1.76-1.89 (m, 4H involving a triplet at 1.87), 3.05 (td, 1H), 4.27-4.33 (m, 1H), 4.45-4.53 (m, 1H), 4.97 (q, 2H), 8.03 (s, 1H)

Production Example 34

0.08 g of sodium hydride (60% oil suspention) was suspended in 3 ml of tetrahydrofuran. 0.5 ml of tetrahydrofuran solution of 0.15 g of 2-butyn-1-ol was added dropwise at room temperature therein, and the mixture was stirred for 10 minutes. Into the mixture was added dropwise 0.5 ml of tetrahydrofuran solution of 0.33 g of 1-(6-chloropyrimidin-4-yl)-2,5-dimethyl hexahydro-1H-azepine at room temperature, and stirred for 4 hours at 60° C. After the reaction mixture was cooled to near room temperature, a saturated ammonium chloride aqueous solution was added therein, and the mixture was extracted with tert-butyl methyl ether three times. The organic layers were washed with a saturated sodium chloride aqueous solution, dried over anhydrous magnesium sulfate and concentrated. The residue was subjected to silica gel column chromatography to obtain 0.17 g of 1-(6-(2-butynyloxy)pyrimidin-4-yl)-2,5-dimethyl hexahydro-1H-azepine (hereinafter, referred to as Compound (34)).

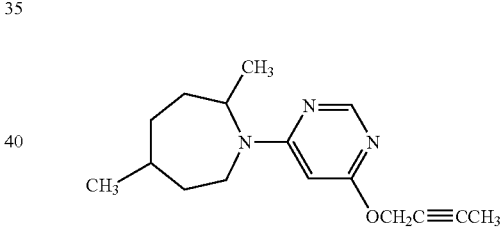

(34)

GC-MS: 273 (M+)

Production Example 35

0.07 g of sodium hydride (60% oil suspention) was suspended in 3 ml of tetrahydrofuran. The 0.5 ml of tetrahydrofuran solution of 0.12 g of 2-butyn-1-ol was added dropwise at room temperature therein, and the mixture was stirred for 10 minutes. Into the mixture was added dropwise 0.5 ml of tetrahydrofuran solution of 0.34 g of 1-(6-chloro-5-fluoropyrimidin-4-yl)-2,5-dimethyl-hexahydro-1H-azepine at room temperature, and stirred for 8 hours at 60° C. After the reaction mixture was cooled to near room temperature, a saturated ammonium chloride aqueous solution was added therein, and the mixture was extracted with tert-butyl methyl ether three times. The organic layers were washed with a saturated sodium chloride aqueous solution, dried over anhydrous magnesium sulfate and concentrated. The residue was subjected to silica gel column chromatography to obtain 0.35 g of 1-(6-(2-butynyloxy)-5-fluoropyrimidin-4-yl)-2,5-dimethyl-hexahydro-1H-azepine (hereinafter, referred to as Compound (35)).

(35)

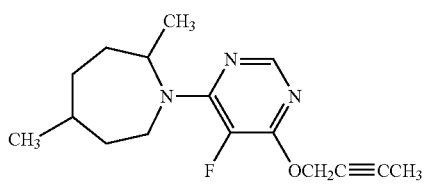

¹H-NMR: 0.89 (d, 3H), 1.04-1.16 (m, 4H involving a doublet at 1.15), 1.25-1.70 (m, 4H), 1.78-1.89 (m, 4H involving a triplet at 1.87), 2.02 (ddd, 1H), 3.01 (dd, 1H), 3.95 (brd, 1H), 4.47-4.58 (br, 1H), 4.97 (q, 2H), 8.03 (s, 1H)

Production Example 36

Into 3 ml of acetonitrile were added 0.20 g of 4-(2-butynyloxy)-6-chloro-5-fluoropyrimidine, 0.41 g of potassium carbonate and 0.20 g of 3,4-dimethylpyrrolidine hydrochloride (cis and trans diastereomer mixture), and the mixture was stirred for 7 hours at 80° C. The reaction mixture was cooled to near room temperature, a saturated ammonium chloride aqueous solution was added therein, and the mixture was extracted with tert-butyl methyl ether three times. The organic layers were washed with a saturated sodium chloride aqueous solution, dried over anhydrous magnesium sulfate and concentrated. The residue was subjected to silica gel column chromatography to obtain 0.20 g of 4-(2-butynyloxy)-6-(3,4-dimethylpyrrolidin-1-yl)-5-fluoropyrimidine (hereinafter, referred to as Compound (36)).

(36)

¹H-NMR: 0.99 (d, 0.6H), 1.08 (d, 2.4H), 1.74-1.88 (m, 4.6H involving a triplet at 1.87), 2.29-2.35 (m, 0.4H), 3.15-3.24 (m, 1.6H), 3.36-3.43 (m, 0.4H), 3.73-3.80 (m, 0.4H), 3.90-3.98 (m, 1.6H), 4.97 (q, 2H), 8.02 (s, 1H)

GC-MS: 263 (M+); 263 (M+)

Production Example 37

Into 3 ml of acetonitrile were added 0.30 g of 4-(2-butynyloxy)-6-chloropyrimidine, 0.68 g of potassium carbonate and 0.33 g of 3,4-dimethylpyrrolidine hydrochloride (cis and trans diastereomer mixture), and the mixture was stirred for 4 hours at 70° C. The reaction mixture was cooled to near room temperature, a saturated ammonium chloride aqueous solution was added therein, and the mixture was extracted with tert-butyl methyl ether three times. The organic layers were washed with a saturated sodium chloride aqueous solution, dried over anhydrous magnesium sulfate and concentrated. The residue was subjected to silica gel column chromatography to obtain 0.42 g of 4-(2-butynyloxy)-6-(3,4-dimethylpyrrolidin-1-yl)pyrimidine (hereinafter, referred to as Compound (37)).

(37)

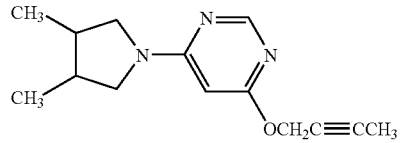

¹H-NMR: 0.99 (d, 1.2H), 1.09 (d, 4.8H), 1.74-1.88 (m, 4.6H involving a triplet at 1.87), 2.14-2.42 (m, 0.4H), 2.80-4.06 (m, 4H), 4.92 (q, 2H), 5.61 (s, 1H), 8.29 (s, 1H)

GC-MS: 245 (M+); 245 (M+)

Production Example 38

Into 2 ml of acetonitrile were added 0.20 g of 4-(2-butynyloxy)-6-chloropyrimidine, 0.45 g of potassium carbonate and 0.24 g of 3,3,5,5-tetramethylpiperidine hydrochloride, and the mixture was stirred for 4 hours at 60° C. The reaction mixture was cooled to near room temperature, a saturated ammonium chloride aqueous solution was added therein, and the mixture was extracted with tert-butyl methyl ether three times. The organic layers were washed with a saturated sodium chloride aqueous solution, dried over anhydrous magnesium sulfate and concentrated. The residue was subjected to silica gel column chromatography to obtain 0.23 g of 4-(2-butynyloxy)-6-(3,3,5,5-tetramethylpiperidino)pyrimidine (hereinafter, referred to as Compound (38)).

(38)

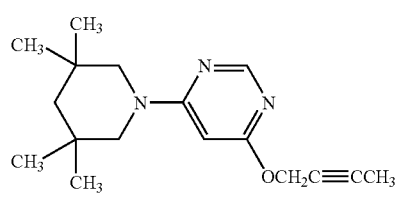

¹H-NMR: 0.97 (s, 12H), 1.32 (s, 2H), 1.87 (t, 3H), 3.30 (s, 4H), 4.91 (q, 2H), 5.88 (s, 1H), 8.27 (s, 1H)

Production Example 39

Into 2 ml of acetonitrile were added 0.20 g of 4-(2-butynyloxy)-6-chloro-5-fluoropyrimidine, 0.54 g of potassium carbonate and 0.30 g of 3,3,5,5-tetramethylpiperidine hydrochloride, and the mixture was stirred for 4 hours at 70° C. The reaction mixture was cooled to near room temperature, a saturated ammonium chloride aqueous solution was added therein, and the mixture was extracted with tert-butyl methyl ether three times. The organic layers were washed with a saturated sodium chloride aqueous solution, dried over anhydrous magnesium sulfate and concentrated. The residue was subjected to silica gel column chromatography to obtain 0.22 g of 4-(2-butynyloxy)-5-fluoro-6-(3,3,5,5-tetramethylpiperidino)pyrimidine (hereinafter, referred to as Compound (39)).

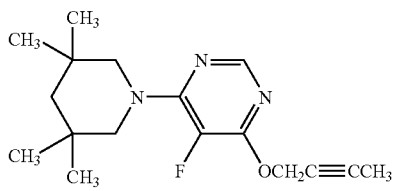

(39)

¹H-NMR: 0.99 (s, 12H), 1.33 (s, 2H), 1.87 (t, 3H), 3.41 (s, 4H), 4.97 (q, 2H), 8.01 (s, 1H)

m.p.: 85.3

Production Example 40

0.07 g of sodium hydride (60% oil suspension) was suspended in 3 ml of tetrahydrofuran. 0.5 ml of tetrahydrofuran solution of 0.11 g of 2-butyn-1-ol was added dropwise at room temperature therein, and the mixture was stirred for 10 minutes. Into the mixture was added dropwise 0.5 ml of tetrahydrofuran solution of 0.30 g of 1-(6-chloropyrimidin-4-yl)-cis-2,6-dimethyl-hexahydro-1H-azepine at room temperature, and stirred for 8 hours at 60° C. After the reaction mixture was cooled to near room temperature, the reaction mixture was poured into a saturated ammonium chloride aqueous solution, and the mixture was extracted with tert-butyl methyl ether three times. The organic layers were washed with a saturated sodium chloride aqueous solution, dried over anhydrous magnesium sulfate and concentrated. The residue was subjected to silica gel column chromatography to obtain 0.25 g of 1-(6-(2-butynyloxy)pyrimidin-4-yl)-cis-2,6-dimethyl-hexahydro-1H-azepine (hereinafter, referred to as Compound (40)).

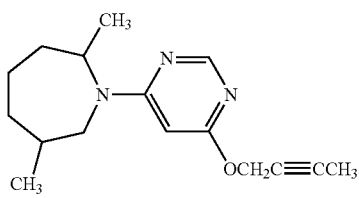

(40)

GC-MS: 273 (M+)

Production Example 41

0.10 g of sodium hydride (60% oil suspention) was suspended in 3 ml of tetrahydrofuran. 0.5 ml of tetrahydrofuran solution of 0.15 g of 2-butyn-1-ol was added dropwise at room temperature therein, and the mixture was stirred for 10 minutes. Into the mixture was added dropwise 0.5 ml of tetrahydrofuran solution of 0.30 g of 1-(6-chloro-5-fluoropyrimidin-4-yl)-cis-2,6-dimethyl-hexahydro-1H-azepine at room temperature, and stirred for 8 hours at 70° C. After the reaction mixture was cooled to near room temperature, the reaction mixture was poured into a saturated ammonium chloride aqueous solution, and the mixture was extracted with tert-butyl methyl ether three times. The organic layers were washed with a saturated sodium chloride aqueous solution, dried over anhydrous magnesium sulfate and concentrated. The residue was subjected to silica gel column chromatography to obtain 0.36 g of 1-(6-(2-butynyloxy)-5-fluoropyrimidin-4-yl)-cis-2,6-dimethyl-hexahydro-1H-azepine (hereinafter, referred to as Compound (41)).

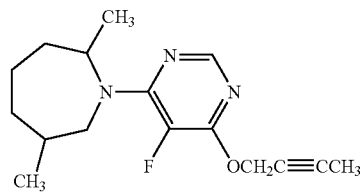

(41)

¹H-NMR: 0.90-1.01 (m, 4H involving a doublet at 0.92), 1.14 (d, 3H), 1.24-1.43 (m, 2H), 1.69-1.89 (m, 6H involving a triplet at 1.87), 2.03-2.11 (m, 1H), 2.86 (td, 1H), 3.68 (dd, 1H), 4.59 (brs, 1H), 4.97 (q, 2H), 8.02 (s, 1H)

GC-MS: 291 (M+)

Production Example 42

0.10 g of sodium hydride (60% oil suspension) was suspended in 3 ml of tetrahydrofuran. 0.5 ml of tetrahydrofuran solution of 0.15 g of 2-butyn-1-ol was added dropwise at room temperature therein, and the mixture was stirred for 10 minutes. Into the mixture was added dropwise 0.5 ml of tetrahydrofuran solution of 0.31 g of 1-(6-chloro-5-fluoropyrimidin-4-yl)-trans-2,6-dimethyl-hexahydro-1H-azepine at room temperature, and stirred for 6 hours at 60° C. After the reaction mixture was cooled to near room temperature, the reaction mixture was poured into a saturated ammonium chloride aqueous solution, and the mixture was extracted with tert-butyl methyl ether three times. The organic layers were washed with a saturated sodium chloride aqueous solution, dried over anhydrous magnesium sulfate and concentrated. The residue was subjected to silica gel column chromatography to obtain 0.34 g of 1-(6-(2-butynyloxy)-5-fluoropyrimidin-4-yl)-trans-2,6-dimethyl-hexahydro-1H-azepine (hereinafter, referred to as Compound (42)).

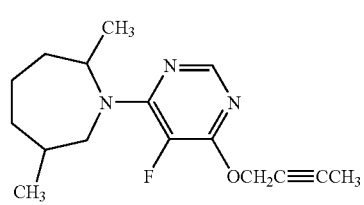

(42)

¹H-NMR: 0.90 (d, 3H), 1.16 (d, 3H), 1.42-1.61 (m, 5H), 1.87 (t, 3H), 1.89-2.05 (m, 2H), 3.35 (d, 1H), 4.14 (dd, 1H), 4.42-4.51 (m, 1H), 4.97 (q, 2H), 8.01 (s, 1H)

GC-MS: 291 (M+)

Production Example 43

0.10 g of sodium hydride (60% oil suspension) was suspended in 3 ml of tetrahydrofuran. 0.5 ml of tetrahydrofuran solution of 0.16 g of 2-butyn-1-ol was added dropwise at room temperature therein, and the mixture was stirred for 10 minutes. Into the mixture was added dropwise 0.5 ml of tetrahydrofuran solution of 0.30 g of 1-(6-chloropyrimidin-4-yl)-trans-2,6-dimethyl hexahydro-1H-azepine at room temperature, and stirred for 5 hours at 60° C. After the reaction mixture was cooled to near room temperature, the reaction mixture was poured into a saturated ammonium chloride aqueous solution, and the mixture was extracted with tert-butyl methyl ether three times. The organic layers were washed with a saturated sodium chloride aqueous solution, dried over anhydrous magnesium sulfate and concentrated. The residue was subjected to silica gel column chromatography to obtain 0.25 g of 1-(6-(2-butynyloxy)pyrimidin-4-yl)-trans-2,6-dimethyl-hexahydro-1H-azepine (hereinafter, referred to as Compound (43)).

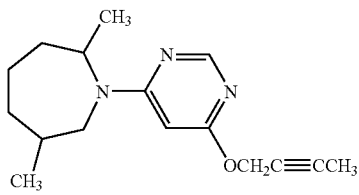

(43)

$^1$H-NMR: 0.90 (d, 3H), 1.12 (d, 3H), 1.42-1.64 (m, 5H), 1.87 (t, 3H), 1.98-2.13 (m, 2H), 3.23 (d, 1H), 3.86-4.26 (br, 2H), 4.91 (q, 2H), 5.85 (s, 1H), 8.01 (s, 1H)
GC-MS: 273 (M+)

Production Example 44

0.02 g of sodium hydride (60% oil suspension) was suspended in 1 ml of tetrahydrofuran. 0.3 ml of tetrahydrofuran solution of 0.02 g of 2-butyn-1-ol was added dropwise at room temperature therein, and the mixture was stirred for 10 minutes. Into the mixture was added dropwise 0.3 ml of tetrahydrofuran solution of 0.05 g of 6-chloro-4-(trans-3,5-dimethylpiperidine)-5-fluoropyrimidine at room temperature, and stirred for 7 hours at 60° C. After the reaction mixture was cooled to near room temperature, the reaction mixture was poured into a saturated ammonium chloride aqueous solution, and the mixture was extracted with tert-butyl methyl ether three times. The organic layers were washed with a saturated sodium chloride aqueous solution, dried over anhydrous magnesium sulfate and concentrated. The residue was subjected to silica gel column chromatography to obtain 0.05 g of 4-(2-butynyloxy)-6-(trans-3,5-dimethylpiperidino)pyrimidine (hereinafter, referred to as Compound (44)).

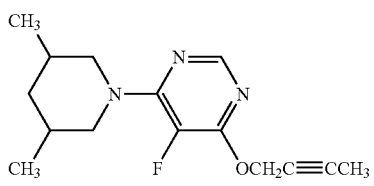

(44)

$^1$H-NMR: 0.95 (d, 6H), 1.49 (t, 2H), 1.87 (t, 3H), 1.94-2.03 (m, 2H), 3.32 (dd, 2H), 3.76 (dd, 2H), 4.97 (q, 2H), 8.02 (s, 1H)

Production Example 45

0.2 g of 4-chloro-6-(2-pentynyloxy)pyrimidine and 0.31 g of octahydroazocine were mixed and left for 2 hours at room temperature. The reaction mixture was subjected to silica gel column chromatography to obtain 0.30 g of 1-(6-(2-butyny-loxy) pyrimidin-4-yl)octahydro-1H-azocine (hereinafter, referred to as Compound (45)).

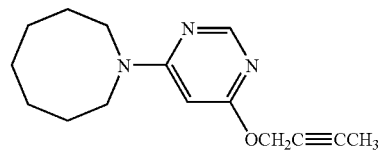

(45)

$^1$H-NMR: 1.44-1.58 (m, 6H), 1.70-1.78 (m, 4H), 1.87 (t, 3H), 3.56 (brs, 4H), 4.92 (q, 2H), 5.75 (s, 1H), 8.30 (s, 1H)

Production Example 46

0.2 g of 4-(2-butynyloxy)-6-chloro-5-fluoropyrimidine and 0.34 g of octahydroazocine were mixed and left for 2 hours at room temperature. The reaction mixture was subjected to silica gel column chromatography to obtain 0.28 g of 1-(6-(2-butynyloxy)-5-fluoropyrimidin-4-yl)octahydro-1H-azocine (hereinafter, referred to as Compound (46)).

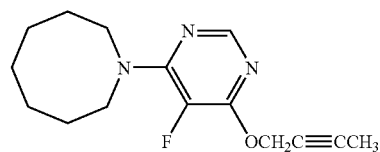

(46)

$^1$H-NMR: 1.50-1.61 (m, 6H), 1.74-1.80 (m, 4H), 1.87 (t, 3H), 3.70 (brt, 4H), 4.97 (q, 2H), 8.03 (s, 1H)

Production Example 47

0.07 g of sodium hydride (60% oil suspension) was suspended in 2 ml of tetrahydrofuran. 0.5 ml of tetrahydrofuran solution of 0.10 g of 2-butyn-1-ol was added dropwise at room temperature therein, and the mixture was stirred for 10 minutes. Into the mixture was added dropwise 0.5 ml of tetrahydrofuran solution of 0.20 g of 1-(6-chloro-5-fluoropyrimidin-4-yl)-2-methyl-hexahydro-1H-azepine at room temperature, and stirred for 6 hours at 60° C. After the reaction mixture was cooled to near room temperature, the reaction mixture was poured into a saturated ammonium chloride aqueous solution, and the mixture was extracted with tert-butyl methyl ether three times. The organic layers were washed with a saturated sodium chloride aqueous solution, dried over anhydrous magnesium sulfate and concentrated. The residue was subjected to silica gel column chromatography to obtain 0.27 g of 1-(6-(2-butynyloxy)-5-fluoropyrimidin-4-yl)-2-methyl-hexahydro-1H-azepine (hereinafter, referred to as Compound (47)).

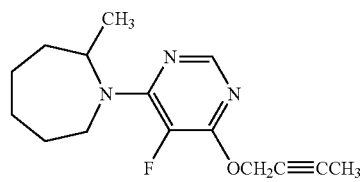

(47)

¹H-NMR: 1.16 (d, 3H), 1.18-1.45 (m, 3H), 1.60-1.89 (m, 7H involving a triplet at 1.87), 2.03-2.12 (m, 1H), 3.05 (t, 1H), 3.99 (d, 1H), 4.48-4.59 (m, 1H), 4.97 (q, 2H), 8.02 (s, 1H)

Production Example 48

0.06 g of sodium hydride (60% oil suspention) was suspended in 1.5 ml of tetrahydrofuran. 0.3 ml of tetrahydrofuran solution of 0.08 g of 2-butyn-1-ol was added dropwise at room temperature therein, and the mixture was stirred for 10 minutes. Into the mixture was added dropwise 0.3 ml of tetrahydrofuran solution of 0.19 g of 6-chloro-4-(cis-2,6-dimethylpiperidino)pyrimidine at room temperature, and stirred for 6 hours at 60° C. After the reaction mixture was cooled to near room temperature, the reaction mixture was poured into a saturated ammonium chloride aqueous solution, and the mixture was extracted with tert-butyl methyl ether three times. The organic layers were washed with a saturated sodium chloride aqueous solution, dried over anhydrous magnesium sulfate and concentrated. The residue was subjected to silica gel column chromatography to obtain 0.20 g of 4-(2-butynyloxy)-6-(cis-2,6-dimethylpiperidino)pyrimidine (hereinafter, referred to as Compound (48)).

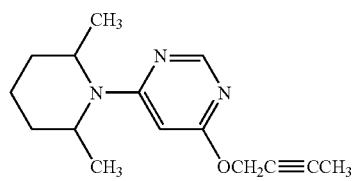

(48)

¹H-NMR: 1.20 (d, 6H), 1.51-1.57 (m, 1H), 1.62-1.75 (m, 4H), 1.82-1.89 (m, 4H, involving a triplet at 1.88), 4.50 (br s, 2H), 4.92 (q, 2H), 5.83 (s, 1H), 8.33 (s, 1H)

Production Example 49

0.05 g of sodium hydride (60% oil suspention) was suspended in 2 ml of tetrahydrofuran. 0.3 ml of tetrahydrofuran solution of 0.09 g of 2-butyn-1-ol was added dropwise at room temperature therein, and the mixture was stirred for 10 minutes. Into the mixture was added dropwise 0.3 ml of tetrahydrofuran solution of 0.21 g of 6-chloro-4-(cis-2,6-dimethylpiperidino)-5-fluoropyrimidine at room temperature, and stirred for 6 hours at 60° C. After the reaction mixture was cooled to near room temperature, the reaction mixture was poured into a saturated ammonium chloride aqueous solution, and the mixture was extracted with tert-butyl methyl ether three times. The organic layers were washed with a saturated sodium chloride aqueous solution, dried over anhydrous magnesium sulfate and concentrated. The residue was subjected to silica gel column chromatography to obtain 0.21 g of 4-(2-butynyloxy)-6-(cis-2,6-dimethylpiperidino)-5-fluoropyrimidine (hereinafter, referred to as Compound (49)).

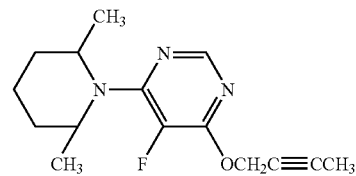

(49)

¹H-NMR: 1.28 (d, 6H), 1.48-1.58 (m, 1H), 1.62-1.79 (m, 4H), 1.82-1.90 (m, 4H involving a triplet at 1.87), 4.68-4.76 (m, 2H), 4.97 (q, 2H), 8.06 (s, 1H)

Production Example 50

0.07 g of sodium hydride (60% oil suspention) was suspended in 2 ml of tetrahydrofuran. 0.3 ml of tetrahydrofuran solution of 0.11 g of 2-butyn-1-ol was added dropwise at room temperature therein, and the mixture was stirred for 10 minutes. Into the mixture was added dropwise 0.3 ml of tetrahydrofuran solution of 0.30 g of 1-(6-chloro-5-fluoropyrimidin-4-yl)-2-ethyl-hexahydro-1H-azepine at room temperature, and stirred for 9 hours at 60° C. After the reaction mixture was cooled to near room temperature, the reaction mixture was poured into a saturated ammonium chloride aqueous solution, and the mixture was extracted with tert-butyl methyl ether three times. The organic layers were washed with a saturated sodium chloride aqueous solution, dried over anhydrous magnesium sulfate and concentrated. The residue was subjected to silica gel column chromatography to obtain 0.31 g of 1-(6-(2-butynyloxy)-5-fluoropyrimidin-4-yl)-2-ethyl-hexahydro-1H-azepine (hereinafter, referred to as Compound (50)).

(50)

¹H-NMR: 0.88 (t, 3H), 1.18-1.88 (m, 12H involving a triplet at 1.87), 2.14-2.21 (m, 1H), 3.01 (dd, 1H), 4.01 (br d, 1H), 4.51 (br s, 1H), 4.97 (q, 2H), 8.00 (s, 1H)

Production Example 51

0.09 g of sodium hydride (60% oil suspention) was suspended in 3 ml of tetrahydrofuran. 0.3 ml of tetrahydrofuran solution of 0.15 g of 2-butyn-1-ol was added dropwise at room temperature therein, and the mixture was stirred for 10 minutes. Into the mixture was added dropwise 0.3 ml of tetrahydrofuran solution of 0.40 g of 4,5-difluoro-6-(3,5-dimethylpiperidino)pyrimidine (cis/trans diastereomer=about 5/1) at room temperature, and stirred for 20 minutes at 0° C. The reaction mixture was poured into a saturated ammonium chloride aqueous solution, and the mixture was extracted with tert-butyl methyl ether three times. The organic layers were washed with a saturated sodium chloride aqueous solution, dried over anhydrous magnesium sulfate and concentrated. The residue was subjected to silica gel column chromatography to obtain 0.46 g of 4-(2-butynyloxy)-5-fluoro-6-(3,5-dimethylpiperidino)pyrimidine (hereinafter, referred to as Compound (51)). Compound (51) had the cis/trans diastereomer originated two methyls on the pyperidine ring. The ratio of the cis/trans diastereomer was about 5/1.

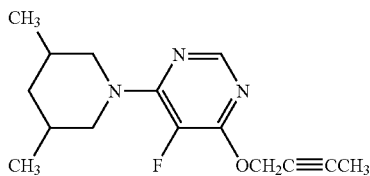
(51)

¹H-NMR: 0.80 (dd, 1H), 0.91 (d, 6H), 1.60-1.72 (m, 2H), 1.81-1.89 (m, 4H, involving a triplet at 1.87), 2.40 (dd, 2H), 4.39 (dd, 2H), 4.97 (q, 2H), 8.04 (s, 1H); 0.94 (s), 1.49 (t), 1.94-2.03 (m), 3.31 (dd), 3.75 (dd), 8.02 (s)

Production Example 52

0.09 g of sodium hydride (60% oil suspension) was suspended in 2 ml of tetrahydrofuran. 0.3 ml of tetrahydrofuran solution of 0.13 g of 2-butyn-1-ol was added dropwise at room temperature therein, and the mixture was stirred for 10 minutes. Into the mixture was added dropwise 0.3 ml of tetrahydrofuran solution of 0.4 g of 5-chloro-2,4-difluoro-6-(3,5-dimethylpiperidino) pyrimidine at 0° C., and stirred for 30 minutes at same temperature. The reaction mixture was poured into a saturated ammonium chloride aqueous solution, and the mixture was extracted with tert-butyl methyl ether three times. The organic layers were washed with a saturated sodium chloride aqueous solution, dried over anhydrous magnesium sulfate and concentrated. The residue was subjected to silica gel column chromatography to obtain 0.20 g of 5-chloro-4-(2-butynyloxy)-2-fluoro-6-(3,5-dimethyl piperidino)pyrimidine (hereinafter, referred to as Compound (52)). Compound (52) had the cis/trans diastereomer originated two methyls on the pyperidine ring. The ratio of the cis/trans diastereomer was about 5/1.

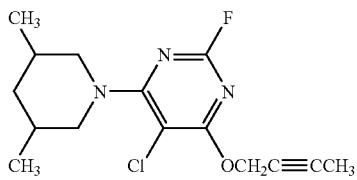
(52)

¹H-NMR: 0.79 (dd, 1H), 0.91 (d, 6H), 1.68-1.89 (m, 6H, involving a triplet at 1.87), 2.40 (dd, 2H), 4.37 (dd, 2H), 4.97 (q, 2H) with peaks due to the minor isomer 0.96 (d), 1.47 (t), 1.98-2.07 (m), 3.37 (dd), 3.68 (dd)

Production Example 53

0.2 g of 4-(2-butynyloxy)-6-chloro-5-fluoropyrimidine and 0.25 g of 1,2,3,6-tetrahydropyridine were mixed and left for 3 hours at room temperature. The reaction mixture was subjected to silica gel column chromatography to obtain 0.25 g of 1-(6-(2-butynyloxy)-5-fluoropyrimidin-4-yl)-1,2,3,6-tetrahydropyridine (hereinafter, referred to as Compound (53)).

(53)

¹H-NMR: 1.87 (t, 3H), 2.22-2.28 (m, 2H), 3.82 (t, 2H), 4.16-4.20 (m, 2H), 4.98 (q, 2H), 5.70-5.75 (m, 1H), 5.86-5.92 (m, 1H), 8.06 (s, 1H)

Production Example 54

0.3 g of 4-chloro-6-(2-butynyloxy)pyrimidine and 0.41 g of 1,2,3,6-tetrahydropyridine were mixed and left for 2 hours at room temperature. The reaction mixture was subjected to silica gel column chromatography to obtain 0.38 g of 1-(6-(2-butynyloxy)pyrimidin-4-yl)-1,2,3,6-tetrahydropyridine (hereinafter, referred to as Compound (54)).

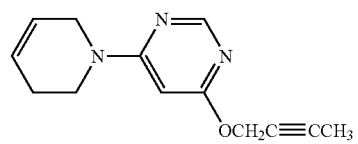
(54)

¹H-NMR: 1.87 (t, 3H), 2.18-2.25 (m, 2H), 3.76 (t, 2H), 3.90-3.94 (m, 2H), 4.93 (q, 2H), 5.72-5.78 (m, 1H), 5.83 (s, 1H), 5.89-5.96 (m, 1H), 8.33 (s, 1H)

Production Example 55

0.3 g of 4-chloro-6-(2-pentenyloxy)pyrimidine and 0.25 g of 1,2,3,6-tetrahydropyridine were mixed and left for 3 hours at room temperature. The reaction mixture was subjected to silica gel column chromatography to obtain 0.23 g of 1-(4-(2-pentynyloxy)pyrimidin-6-yl)pyridine (hereinafter, referred to as Compound (55)).

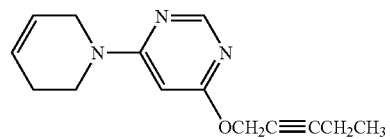
(55)

¹H-NMR: 1.07 (t, 3H), 2.13-2.20 (m, 4H), 3.68 (t, 2H), 3.82-3.85 (m, 2H), 4.86 (t, 2H), 5.63-5.69 (m, 1H), 5.73 (s, 1H), 5.81-5.86 (m, 1H), 8.23 (s, 1H)

Next, the production of the intermediates for the present compound is illustrated as the Reference Production Examples.

Reference Production Example 1

0.61 g of sodium hydride (60% oil suspension) was suspended in 20 ml of tetrahydrofuran. 1 ml of tetrahydrofuran solution of 0.73 g of 2-butyn-1-ol was added dropwise at 0° C. therein, and the mixture was stirred for 10 minutes. Into the mixture was added dropwise 5 ml of tetrahydrofuran solution of 1.75 g of 4,6-dichloro-5-fluoropyrimidine, and stirred for 90 minutes at 0° C. The reaction mixture was poured into a saturated ammonium chloride aqueous solution, and the mixture was extracted with tert-butyl methyl ether three times. The organic layers were washed with a saturated sodium chloride aqueous solution, dried over anhydrous magnesium sulfate and concentrated. The residue was subjected to silica gel column chromatography to obtain 1.8 g of 4-(2-butynyloxy)-6-chloro-5-fluoropyrimidine.

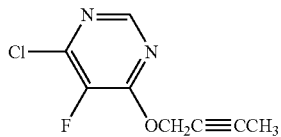

$^1$H-NMR: 1.79 (t, 3H), 5.00 (q, 2H), 8.29 (s, 1H)

Reference Production Example 2

1.05 g of sodium hydride (60% oil suspention) was suspended in 24 ml of tetrahydrofuran. 8 ml of tetrahydrofuran solution of 1.42 g of 2-butyn-1-ol was added dropwise at room temperature therein slowly, and the mixture was stirred for 20 minutes. Into the mixture was added dropwise 8 ml of tetrahydrofuran solution of 3 g of 4,6-dichloropyrimidine at 0° C. slowly, and stirred for 4 hours. The reaction mixture was poured into a saturated ammonium chloride aqueous solution, and the mixture was extracted with chloroform three times. The organic layers were washed with water, dried over anhydrous magnesium sulfate and concentrated. The residue was subjected to silica gel column chromatography to obtain 3.16 g of 4-chloro-6-(2-butynyloxy)pyrimidine.

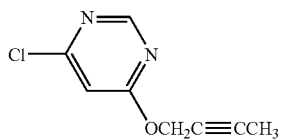

mp.: 43.5° C.

Reference Production Example 3

0.56 g of sodium hydride (60% oil suspention) was suspended in 18 ml of tetrahydrofuran. 2 ml of tetrahydrofuran solution of 0.8 g of 2-butyn-1-ol was added dropwise at room temperature therein slowly, and the mixture was stirred for 20 minutes. Into the mixture was added dropwise 5 ml of tetrahydrofuran solution of 3 g of 4,5,6-trichloropyrimidine at 0° C. slowly, and stirred for 2 hours. The reaction mixture was poured into a saturated ammonium chloride aqueous solution, and the mixture was extracted with ethyl acetate three times. The organic layers were washed with a saturated sodium chloride aqueous solution, dried over anhydrous magnesium sulfate and concentrated. The residue was subjected to silica gel column chromatography to obtain 2.23 g of 4,5-dichloro-6-(2-butynyloxy)pyrimidine.

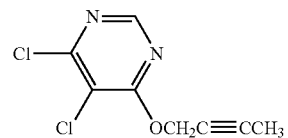

$^1$H-NMR: 1.88 (t, 3H), 5.08 (q, 2H), 8.48 (s, 1H)

Reference Production Example 4

0.32 g of sodium hydride (60% oil suspention) was suspended in 12 ml of tetrahydrofuran. 2 ml of tetrahydrofuran solution of 0.43 g of 2-butyn-1-ol was added dropwise at room temperature therein slowly, and the mixture was stirred for 20 minutes. Into the mixture was added dropwise 2 ml of tetrahydrofuran solution of 1 g of 4,6-dichloro-5-methylpyrimidine at 0° C. slowly, and stirred for 2 hours. The reaction mixture was poured into a saturated ammonium chloride aqueous solution, and the mixture was extracted with tert-butyl methyl ether three times. The organic layers were washed with water, dried over anhydrous magnesium sulfate and concentrated. The residue was subjected to silica gel column chromatography to obtain 1.1 g of 4-chloro-6-(2-butynyloxy)-5-methylpyrimidine.

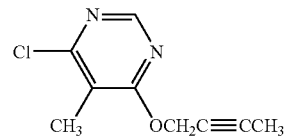

$^1$H-NMR: 1.88 (t, 3H), 2.26 (s, 3H), 5.00 (q, 2H), 8.44 (s, 1H)

Reference Production Example 5

0.58 g of sodium hydride (60% oil suspention) was suspended in 20 ml of tetrahydrofuran. 1 ml of tetrahydrofuran solution of 0.88 g of 2-pentyn-1-ol was added dropwise at 0° C. therein slowly, and the mixture was stirred for 10 minutes. Into the mixture was added dropwise 5 ml of tetrahydrofuran solution of 2 g of 4,6-dichloro-5-fluoropyrimidine at 0° C., and stirred for 70 minutes. The reaction mixture was poured into a saturated ammonium chloride aqueous solution, and the mixture was extracted with tert-butyl methyl ether three times. The organic layers were washed with water, dried over anhydrous magnesium sulfate and concentrated. The residue was subjected to silica gel column chromatography to obtain 2.31 g of 4-chloro-5-fluoro-6-(2-pentynyloxy)pyrimidine.

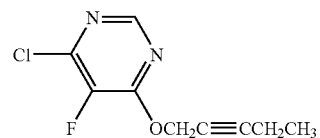

$^1$H-NMR: 1.15 (t, 3H), 2.24 (qt, 2H), 5.09 (t, 2H), 8.36 (s, 1H)

Reference Production Example 6

0.3 g of 4,6-dichloropyrimidine and 0.34 g of 3,5-dimethylpiperidine (cis/trans diastereomer=about 3/1) were mixed and left for 5 hours at room temperature. The reaction mixture was subjected to silica gel column chromatography to obtain 0.3 g of 4-chloro-6-(3,5-dimethylpiperidino)pyrimidine. This compound had the cis/trans diastereomer originated two methyls on the pyperidine ring. The ratio of the cis/trans diastereomer was about 3.1/1.

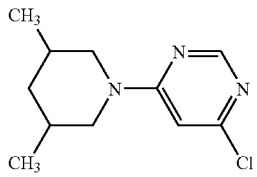

$^1$H-NMR: 0.85 (dd, 1H), 0.95 (d, 6H), 1.56-1.68 (m, 2H), 1.84-1.89 (m, 1H), 2.37 (dd, 2H), 6.49 (s, 1H), 8.34 (s, 1H); 0.95 (d), 1.90-2.25 (m), 3.20-3.31 (m) 3.59-3.76 (m), 6.47 (s), 8.32 (s)

Reference Production Example 7

0.2 g of 4,6-dichloro-5-fluoropyrimidine and 0.41 g of 3,5-dimethylpiperidine (cis/trans diastereomer=about 3/1) were mixed and left for 30 minutes at room temperature. The reaction mixture was subjected to silica gel column chromatography to obtain 0.1 g of 4-chloro-6-(cis-3,5-dimethyl piperidino)-5-fluoropyrimidine and 0.05 g of 4-chloro-6-(trans-3,5-dimethylpiperidino)pyrimidin.

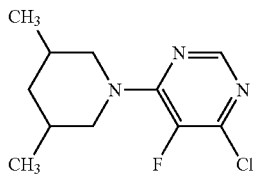

Cis Diastereomer:

$^1$H-NMR: 0.84 (dd, 1H), 0.93 (d, 6H), 1.64-1.78 (m, 2H), 1.84-1.92 (m, 1H), 2.46 (dd, 2H), 4.48 (d, 2H), 8.11 (s, 1H)

Trans Diastereomer:

$^1$H-NMR: 0.96 (d, 6H), 1.51 (t, 2H), 1.96-2.06 (m, 2H), 3.40 (dd, 2H), 3.83 (dd, 2H), 8.10 (s, 1H)

Reference Production Example 8

0.07 g of sodium hydride (60% oil suspension) was suspended in 3 ml of tetrahydrofuran. 1 ml of tetrahydrofuran solution of 0.14 g of 2-ethylpiperidine was added dropwise at room temperature therein slowly, and the mixture was stirred for 10 minutes. Into the mixture was added dropwise 1 ml of tetrahydrofuran solution of 0.2 g of 4,6-dichloro-5-fluoropyrimidine at room temperature, and stirred for 4 hours. The reaction mixture was poured into a saturated ammonium chloride aqueous solution, and the mixture was extracted with tert-butyl methyl ether three times. The organic layers were washed with water, dried over anhydrous magnesium sulfate and concentrated. The residue was subjected to silica gel column chromatography to obtain 0.22 g of 4-chloro-6-(2-ethylpiperidino)-5-fluoropyrimidine.

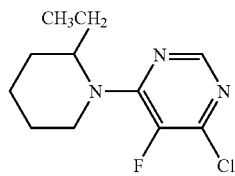

$^1$H-NMR: 0.89 (t, 3H), 1.50-1.76 (m, 7H), 1.78-1.91 (m, 1H), 3.08 (td, 1H), 4.35-4.42 (m, 1H), 4.54-4.62 (m, 1H), 8.10 (s, 1H)

Reference Production Example 9

Into 3 ml of acetnitrile were added 0.2 g of 4,6-dichloropyrimidine, 0.56 g of potassium carbonate and 0.26 g of 2,5-dimethylhexahydro-1H-azepine hydrochloride, and the mixture was stirred for 3 hours at 80° C. The reaction mixture was cooled to near room temperature, a saturated ammonium chloride aqueous solution was added therein, and the mixture was extracted with tert-butyl methyl ether three times. The organic layers were washed with a saturated sodium chloride aqueous solution, dried over anhydrous magnesium sulfate and concentrated. The residue was subjected to silica gel column chromatography to obtain 0.3 g of 1-(6-chloropyrimidin-4-yl)-2,5-dimethylhexahydro-1H-azepine.

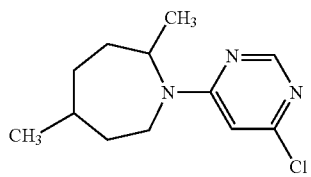

$^1$H-NMR: 0.84-2.10 (m, 13H), 2.98 (brt, 0.4H), 3.22-3.34 (m, 1.2H), 3.60-3.72 (m, 0.4H), 4.29 (brd, 0.4H), 4.71-4.83 (m, 0.6H), 6.36 (s, 0.6H), 6.44 (s, 0.4H), 8.36 (s, 1H)

GC-MS: 239 (M+)

Reference Production Example 10

Into 3 ml of acetnitrile were added 0.2 g of 4,6-dichloro-5-fluoropyrimidine, 0.50 g of potassium carbonate and 0.24 g of 2,5-dimethylhexahydro-1H-azepine hydrochloride, and the mixture was stirred for 5 hours at 80° C. The reaction mixture was cooled to near room temperature, a saturated ammonium chloride aqueous solution was added therein, and the mixture was extracted with tert-butyl methyl ether three times. The organic layers were washed with a saturated sodium chloride aqueous solution, dried over anhydrous magnesium sulfate and concentrated. The residue was subjected to silica gel column chromatography to obtain 0.3 g of 1-(6-chloro-5-fluoro pyrimidin-4-yl)-2,5-dimethylhexahydro-1H-azepine.

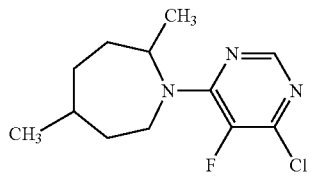

$^1$H-NMR: 0.84-1.59 (m, 10H involving a doublet at 0.92), 1.66-1.71 (m, 1H), 1.84-1.92 (m, 1H), 2.05 (ddd, 1H), 3.16 (brt, 1H), 3.96 (br, 1H), 4.58 (br, 1H), 8.11 (s, 1H)

GC-MS: 257 (M+)

Reference Production Example 11

Into 4 ml of acetnitrile were added 0.3 g of 4,6-dichloropyrimidine, 0.83 g of potassium carbonate and 0.43 g of cis-2,6-dimethylhexahydro-1H-azepine hydrochloride, and the mixture was stirred for 4 hours at 60° C. The reaction mixture was cooled to near room temperature, a saturated ammonium chloride aqueous solution was added therein, and the mixture was extracted with tert-butyl methyl ether three times. The organic layers were washed with a saturated sodium chloride aqueous solution, dried over anhydrous magnesium sulfate and concentrated. The residue was subjected to silica gel column chromatography to obtain 0.3 g of 1-(6-chloropyrimidin-4-yl)-cis-2,6-dimethylhexahydro-1H-azepine.

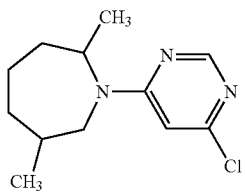

$^1$H-NMR: 0.92-2.13 (m, 13H), 2.71 (dd, 0.4H), 2.98-3.09 (m, 1.2H), 3.60-3.69 (m, 0.4H), 4.06 (d, 0.4H), 4.74-4.85 (m, 0.6H), 6.25 (s, 0.6H), 6.40 (s, 0.4H), 8.35 (s, 1H)

GC-MS: 239 (M+)

Reference Production Example 12

Into 3 ml of acetnitrile were added 0.2 g of 4,6-dichloro-5-fluoropyrimidine, 0.50 g of potassium carbonate and 0.27 g of cis-2,6-dimethylhexahydro-1H-azepine hydrochloride, and the mixture was stirred for 2 hours at 60° C. The reaction mixture was cooled to near room temperature, a saturated ammonium chloride aqueous solution was added therein, and the mixture was extracted with tert-butyl methyl ether three times. The organic layers were washed with a saturated sodium chloride aqueous solution, dried over anhydrous magnesium sulfate and concentrated. The residue was subjected to silica gel column chromatography to obtain 0.3 g of 1-(6-chloro-5-fluoropyrimidin-4-yl)-cis-2,6-dimethyl-hexahydro-1H-azepine

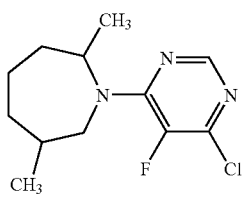

$^1$H-NMR: 0.90-1.04 (m, 4H involving a doublet at 0.95), 1.10-1.32 (m, 4H), 1.36-1.48 (m, 1H), 1.71-1.90 (m, 3H), 2.04-2.14 (m, 1H), 2.91 (brt, 1H), 3.70 (brs, 1H), 4.42-4.82 (br, 1H) 8.09 (d, 1H)

GC-MS: 257 (M+)

Reference Production Example 13

Into 3 ml of acetnitrile were added 0.2 g of 4,6-dichloro-5-fluoropyrimidine, 0.50 g of potassium carbonate and 0.27 g of trans-2,6-dimethylhexahydro-1H-azepine hydrochloride, and the mixture was stirred for 2 hours at 60° C. The reaction mixture was cooled to near room temperature, a saturated ammonium chloride aqueous solution was added therein, and the mixture was extracted with tert-butyl methyl ether three times. The organic layers were washed with a saturated sodium chloride aqueous solution, dried over anhydrous magnesium sulfate and concentrated. The residue was subjected to silica gel column chromatography to obtain 0.31 g of 1-(6-chloro-5-fluoropyrimidin-4-yl)-trans-2,6-dimethyl-hexahydro-1H-azepine.

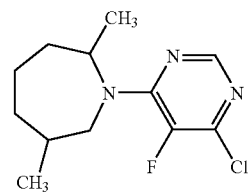

$^1$H-NMR: 0.92 (d, 3H), 1.19 (d, 3H) 1.44-1.65 (m, 5H), 1.94-2.11 (m, 2H), 3.41 (d, 1H), 4.17 (brd, 1H), 4.47-4.56 (m, 1H) 8.10 (d, 1H)

Reference Production Example 14

Into 3 ml of acetnitrile were added 0.2 g of 4,6-dichloropyrimidine, 0.56 g of potassium carbonate and 0.31 g of trans-2,6-dimethylhexahydro-1H-azepine hydrochloride, and the mixture was stirred for 2 hours at 60° C. The reaction mixture was cooled to near room temperature, a saturated ammonium chloride aqueous solution was added therein, and the mixture was extracted with tert-butyl methyl ether three times. The organic layers were washed with a saturated sodium chloride aqueous solution, dried over anhydrous magnesium sulfate and concentrated. The residue was subjected to silica gel column chromatography to obtain 0.30 g of 1-(6-chloropyrimidin-4-yl)-trans-2,6-dimethylhexahydro-1H-azepine.

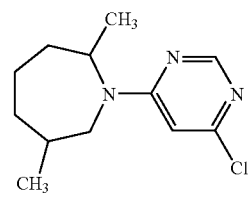

$^1$H-NMR: 0.91 (d, 3H), 1.14 (d, 3H) 1.42-1.68 (m, 7H), 2.04 (ddd, 1H), 2.10-2.18 (m, 1H), 3.26 (brs, 1H), 6.47 (s, 1H) 8.33 (s, 1H)

GC-MS: 239 (M+)

Reference Production Example 15

Into 6 ml of tetrahydrofuran solution of 0.5 g of 2,4,6-trifluoro-5-chloropyrimidine was added dropwise 0.34 g or 3,5-dimethylpiperidine (cis/trans diastreomer=about 4/1) at room temperature, and the mixture was stirred for one-and-half hour at same temperature. The reaction mixture was subjected to silica gel column chromatography to obtain 0.56 g of 5-chloro-2,4-difluoro-6-(3,5-dimethylpiperidino)pyrimidine. This compound had the cis/trans diastereomer originated two ethyls on the pyperidine ring. The ratio of the cis/trans diastereomer was about 5/1.

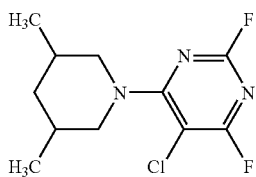

¹H-NMR: 0.87 (dd, 1H), 0.94 (d, 6H), 1.70-1.82 (m, 2H), 1.86-1.94 (m, 1H), 2.47 (dd, 2H), 4.56 (dd, 2H) with peaks due to the minor isomer 0.97 (d), 1.51 (t), 2.02-2.11 (m), 3.51 (dd).3.82 (dd)

Reference Production Example 16

Into 80 ml of ethanol were suspended 5 g of 2,6-dimethylcyclohexanone and 5.51 g of hydroxylamine hydrochloride, 9.4 g of pyridine was added dropwise at 0° C., and the mixture was stirred for 4 hours at room temperature. The reaction mixture was concentrated, water was added to the residue, the mixture was extracted with ethyl acetate three times. The organic layers were washed with a saturated sodium chloride aqueous solution, dried over anhydrous magnesium sulfate and concentrated. The residue was subjected to silica gel column chromatography to obtain 3.1 g of cis-2,6-dimethyl cyclohexanone oxime and 1.3 g of trans-2,6-dimethylcyclohexanone oxime.

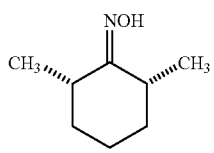

Cis Diastereomer:
¹H-NMR: 1.19 (d, 3H), 1.21 (d, 3H), 1.42-1.51 (m, 1H), 1.53-1.85 (m, 5H), 2.58-2.67 (m, 1H), 3.39-3.48 (m, 1H), 8.58 (brs, 1H)

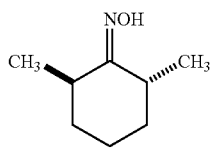

Trans Diastereomer:
¹H-NMR: 1.08 (d, 3H), 1.12 (d, 3H), 1.14-1.25 (m, 1H), 1.52-1.72 (m, 4H), 1.83-1.91 (m, 1H), 2.32-2.46 (m, 1H), 3.64-3.69 (m, 1H), 8.81 (s, 1H)

Reference Production Example 17

Into 40 ml of xylene were added 3.1 g of cis-2,6-dimethylcyclohexanone oxime and 12 g of polyphosphoric acid, the mixture was stirred for 10 hours at 100° C. The reaction mixture was cooled to near room temperature, poured into ice-water. Sodium carbonate was added to the mixture, and the mixture was extracted with ethyl acetate three times. The organic layers was washed with a saturated sodium chloride aqueous solution, dried over anhydrous magnesium sulfate and concentrated. The residue was subjected to silica gel column chromatography to obtain 2.5 g of cis-3,7-dimethylhexahydro-1H-azepine-2-one.

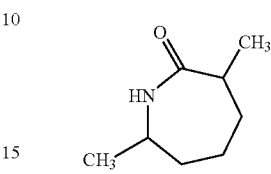

¹H-NMR: 1.31 (d, 3H), 1.91 (d, 3H), 1.26-1.36 (m, 1H), 1.40-1.51 (m, 1H), 1.60-1.76 (3H), 1.91-1.97 (m, 1H), 2.48-2.56 (m, 1H), 3.49-3.58 (m, 1H), 5.36 (brs, 1H)

Reference Production Example 18

Into 20 ml of tetrahydrofuran was suspended 0.54 g of lithium aluminiumhydride, 1 g of cis-3,7-dimethylhexahydro-1H-azepine-2-one was added therein little by little at 0° C., and the mixture was stirred for 10 hours under the reflux condition. The reaction mixture was cooled to 0° C., 0.54 ml of water, 0.54 ml of 15% sodium hydroxide aqueous solution and 1.62 ml of water was added therein successively, the mixture was stirred for 30 minutes. Into the mixture was added magnesium sulfate, the mixture was filtered over Celite. Into the filtrate was added 8.4 ml of 1N hydrogen chloride/diethyl ether at 0° C., and the mixture was stirred for 1 hour, concentrated to obtain 1 g of cis-2,6-dimethylhexahydro-1H-azepine hydrochloride.

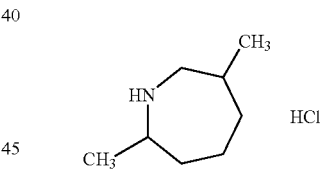

¹H-NMR: 1.01 (d, 3H), 1.21-1.33 (m, 1H), 1.48 (d, 3H), 1.60-1.72 (m, 2H), 1.79-2.01 (m, 3H), 2.12-2.21 (m, 1H), 2.77-2.88 (m, 1H), 3.22 (brd, 1H), 3.54 (brs, 1H), 9.44 (br, 2H)

Reference Production Example 19

Into 20 ml of xylene were added 1.3 g of trans-2,6-dimethylcyclohexanone oxime and 6 g of polyphosphoric acid, the mixture was stirred for 10 hours at 100° C. The reaction mixture was cooled to near room temperature, poured into ice-water. Sodium carbonate was added to the mixture, and the mixture was extracted with ethyl acetete three times. The organic layers was washed with a saturated sodium chloride aqueous solution, dried over anhydrous magnesium sulfate and concentrated. The residue was subjected to silica gel column chromatography to obtain 1.2 g of trans-3,7-dimethylhexahydro-1H-azepine-2-one.

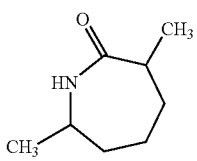

¹H-NMR: 1.21 (d, 3H), 1.25 (d, 3H), 1.43-1.63 (m, 2H), 1.76 (brs, 4H), 2.70-2.79 (m, 1H), 3.51-3.62 (m, 1H), 5.71 (brs, 1H)

Reference Production Example 20

Into 20 ml of tetrahydrofuran was suspended 0.54 g of lithium aluminiumhydride, 1 g of trans-3,7-dimethylhexahydro-1H-azepine-2-one was added therein little by little at 0° C., and the mixture was stirred for 10 hours under the reflux condition. The reaction mixture was cooled to 0° C., 0.54 ml of water, 0.54 ml of 15% sodium hydroxide aqueous solution and 1.62 ml of water was added therein successively, the mixture was stirred for 30 minutes. Into the mixture was added magnesium sulfate, the mixture was filtered over Celite. Into the filtrate was added 8.4 ml of 1N hydrogen chloride/diethyl ether at 0° C., and the mixture was stirred for 1 hour, concentrated to obtain 0.98 g of trans-2,6-dimethyl hexahydro-1H-azepine hydrochloride.

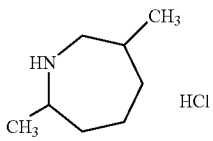

¹H-NMR: 0.98 (d, 3H), 1.27-1.39 (m, 1H), 1.53 (d, 3H), 1.65-1.75 (m, 1H), 1.81-1.99 (m, 4H), 2.42 (brs, 1H), 2.56-2.66 (m, 1H), 3.30-3.41 (m, 2H), 9.06 (brs, 1H), 9.62 (br, 1H)

Reference Production Example 21

The mixture of 10 g of 2,2-dimethylglutaric acid and 37.5 g of urea was stirred for 8 hours at 160° C. Into the reaction mixture was added water at 100° C., and the mixture was cooled to near room temperature. The mixture was extracted with ethyl acetate three times. The organic layers were washed with a saturated sodium chloride aqueous solution, dried over anhydrous magnesium sulfate and concentrated. The residue was subjected to silica gel column chromatography to obtain 7.6 g of 3,3-dimethylpiperidin-2,6-dione.

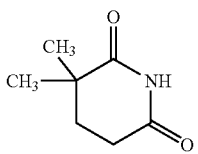

¹H-NMR: 1.29 (s, 6H), 1.83-1.88 (m, 2H), 2.64-2.68 (m, 2H), 7.94 (brs, 1H)

Reference Production Example 22

Into 15 ml of tetrahydrofuran was suspended 0.54 g of lithium aluminiumhydride, 1 g of 3,3-dimethylpiperidin-2,6-dione was added therein little by little at 0° C., and the mixture was stirred for 10 hours under the reflux condition. The reaction mixture was cooled to 0° C., 0.54 ml of water, 0.54 ml of 15% sodium hydroxide aqueous solution and 1.61 ml of water was added therein successively, the mixture was stirred for 30 minutes. Into the mixture was added magnesium sulfate, the mixture was filtered over Celite. Into the filtrate was added 10.6 ml of 1N hydrogen chloride/diethyl ether at 0° C., and the mixture was stirred for 1 hour, concentrated to obtain 0.7 g of 3,3-dimethylpiperidine hydrochloride.

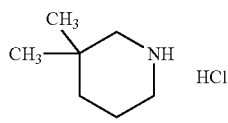

¹H-NMR: 1.12 (s, 6H), 1.45-1.48 (m, 2H), 1.84-1.91 (m, 2H), 2.85 (brs, 2H), 3.09 (brs, 2H), 9.31 (br, 2H)

Reference Production Example 23

The mixture of 5 g of 2,3-dimethylsuccinic acid and 20 g of urea was stirred for 10 hours at 160° C. Into the reaction mixture was added water at 100° C., and the mixture was cooled to near room temperature. The mixture was extracted with ethyl acetate three times. The organic layers were washed with a saturated sodium chloride aqueous solution, dried over anhydrous magnesium sulfate and concentrated. The residue was subjected to silica gel column chromatography to obtain 4.7 g of the cis/trans diastereomer mixture of 3,4-dimethyl pyrrolidin-2,5-dione.

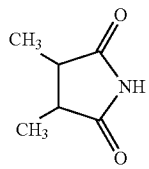

¹H-NMR: 1.24 (d, 1.2H), 1.35 (d, 4.8H), 2.45-2.53 (m, 1.6H), 2.95-3.04 (m, 0.4H) 8.01 (br, 1H)

Reference Production Example 24

Into 15 ml of tetrahydrofuran was suspended 1.19 g of lithium aluminiumhydride, 1 g of 3,4-dimethylpyrrolidine-2,5-dione was added therein little by little at 0° C., and the mixture was stirred for 10 hours under the reflux condition. The reaction mixture was cooled to 0° C., 1.2 ml of water, 1.2 ml of 15% sodium hydroxide aqueous solution and 3.6 ml of water was added therein successively, the mixture was stirred for 30 minutes. Into the mixture was added magnesium sulfate, the mixture was filtered over Celite. Into the filtrate was added 9.44 ml of 1N hydrogen chloride/diethyl ether at 0° C., and the mixture was stirred for 1 hour, concentrated to obtain 0.62 g of the cis/trans diastereomer mixture of 3,4-dimethylpyrrolidine hydrochloride.

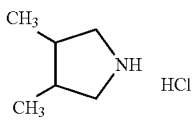

¹H-NMR: 1.01 (d, 1.2H), 1.08 (d, 4.8H), 1.79-1.91 (m, 1.6H), 2.36-2.43 (m, 0.4H), 2.83 (dd, 1.6H), 2.97 (dd, 0.4H), 3.41 (dd, 0.4H), 3.52 (dd, 1.6H), 6.52 (br, 1H)

Reference Production Example 25

The mixture of 2.6 g of tetramethylglutaric acid and 8.3 g of urea was stirred for 10 hours at 160° C. Into the reaction mixture was added water at 100° C., and the mixture was cooled to near room temperature. The mixture was extracted with ethyl acetate three times. The organic layers were washed with a saturated sodium chloride aqueous solution, dried over anhydrous magnesium sulfate and concentrated. The residue was subjected to silica gel column chromatography to obtain 2.3 g of 3,3,5,5-tetramethylpiperidin-2,6-dione.

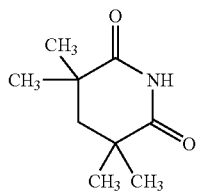

¹H-NMR: 1.31 (s, 12H), 1.81 (s, 2H), 7.75 (br, 1H)

Reference Production Example 26

Into 13 ml of tetrahydrofuran was suspended 0.90 g of lithium aluminiumhydride, 1 g of 3,3,5,5-tetramethyl piperidin-2,6-dione was added therein little by little at 0° C. and the mixture was stirred for 10 hours under the reflux condition. The reaction mixture was cooled to 0° C., 0.9 ml of water, 0.9 ml of 15% sodium hydroxide aqueous solution and 2.7 ml of water was added therein successively, the mixture was stirred for 30 minutes. Into the mixture was added magnesium sulfate, the mixture was filtered over Celite. Into the filtrate was added 7 ml of 1N hydrogen chloride/diethyl ether at 0° C., and the mixture was stirred for 1 hour, concentrated to obtain 0.59 g of 3,3,5,5-tetramethylpiperidine hydrochloride.

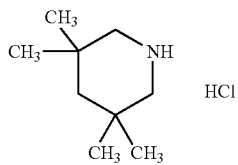

¹H-NMR: 1.71 (s, 12H), 1.97 (brs, 2H), 2.81-2.84 (m, 4H), 9.49 (br, 2H)

Reference Production Example 27

The mixture of 10 g of 3,3-dimethylsuccinic acid and 102.7 g of urea was stirred for 10 hours at 160° C. Into the reaction mixture was added water at 100° C., and the mixture was cooled to near room temperature. The mixture was extracted with ethyl acetate three times. The organic layers were washed with a saturated sodium chloride aqueous solution, dried over anhydrous magnesium sulfate and concentrated. The residue was subjected to silica gel column chromatography to obtain 7.8 g of 3,3-dimethylpyrrolidin-2,5-dione.

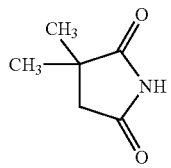

¹H-NMR: 1.35 (s, 6H), 2.60 (s, 2H), 8.36 (br, 1H)

Reference Production Example 28

Into 15 ml of tetrahydrofuran was suspended 0.96 g of lithium aluminiumhydride, 1 g of 3,3-dimethylpyrrolidine-2,5-dione was added therein little by little at 0° C., and the mixture was stirred for 12 hours under the reflux condition. The reaction mixture was cooled to 0° C., 0.96 ml of water, 0.96 ml of 15% sodium hydroxide aqueous solution and 2.88 ml of water was added therein successively, the mixture was stirred for 30 minutes. Into the mixture was added magnesium sulfate, the mixture was filtered over Celite. Into the filtrate was added 15.74 ml of 1N hydrogen chloride/diethyl ether at 0° C., and the mixture was stirred for 1 hour, concentrated to obtain 0.45 g of 3,3-dimethylpyrrolidine hydrochloride.

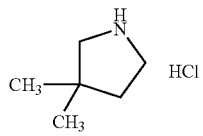

¹H-NMR: 1.19 (s, 6H), 1.79-1.84 (m, 2H), 3.01-3.07 (m, 2H), 3.43-3.51 (m, 2H), 9.37 (br, 2H)

Reference Production Example 29

0.4 g of 4,6-dichloro-5-fluoropyrimidine and 0.61 g of 2-ethylhexahydro-1H-azepine were mixed and left for 1 hour at room temperature. The reaction mixture was subjected to silica gel column chromatography to obtain 0.6 g of 1-(6-chloro-5-fluoropyrimidin-4-yl)-2-ethylhexahydro-1H-azepine.

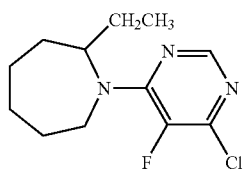

¹H-NMR: 0.90 (t, 3H), 1.16-1.41 (m, 3H), 1.48-1.68 (m, 3H), 1.78-1.83 (m, 3H), 2.17-2.24 (m, 1H), 3.07 (br t, 1H), 4.08 (br s, 1H), 4.40-4.80 (br, 1H), 8.09 (s, 1H)

Reference Production Example 30

0.5 g of 4,6-dichloropyrimidine and 0.76 g of cis-2,6-dimethylpiperidine were mixed and stirred for 10 hours at 90°

C. The reaction mixture was subjected to silica gel column chromatography to obtain 0.21 g of 4-chloro-6-(cis-2,6-dimethylpiperidino)pyrimidine.

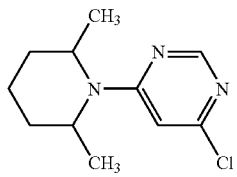

¹H-NMR: 1.23 (d, 6H), 1.55-1.59 (m, 1H), 1.67-1.73 (m, 4H), 1.82-1.90 (m, 1H), 4.48-4.65 (br, 2H), 6.44 (s, 1H), 8.38 (s, 1H)

Reference Production Example 31

0.25 g of 4,6-dichloro-5-fluoropyrimidine and 0.34 g of cis-2,6-dimethylpiperidine were mixed and stirred for 11 hours at 70° C. The reaction mixture was subjected to silica gel column chromatography to obtain 0.21 g of 4-chloro-6-(cis-2,6-dimethylpiperidino)-5-fluoropyrimidine.

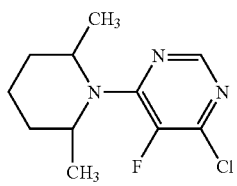

¹H-NMR: 1.32 (d, 6H), 1.53-1.58 (m, 1H), 1.67-1.81 (m, 4H), 1.82-1.94 (m, 1H), 4.83 (br s, 2H), 8.14 (s, 1H)

Reference Production Example 32

Into 6 ml of toluene solution of 0.5 g of 4,5,6-trifluoropyrimidine was added dropwise 1 ml toluene solution of 0.51 g of 3,5-dimethylpiperidine (cis/trans diastereomer=about 4/1) at 0° C., and the mixture was stirred for one-and-half hour at same temperature. The reaction mixture was subjected to silica gel column chromatography to obtain 0.83 g of 4,5-difluoro-6-(3,5-dimethylpiperidino)pyrimidine. This compound had the cis/trans diastereomers originated two methyls on the piperidine ring. The ratio of the cis/trans diastereomer was about 5/1.

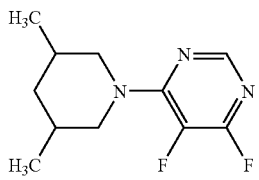

¹H-NMR: 0.84 (dd, 1H), 0.94 (d, 6H), 1.64-1.75 (m, 2H), 1.88 (br d, 1H), 2.46 (dd, 2H), 4.46-4.51 (m, 2H), 8.02 (s, 1H) with peaks due to the minor isomer 0.95 (d), 1.52 (t), 1.96-2.08 (m), 3.39 (dd). 3.83 (dd), 8.00 (s)

Reference Production Example 33

Into 2 ml of acetnitrile were added 0.13 g of 4,6-dichloro-5-fluoropyrimidine, 0.14 g of potassium carbonate and 0.10 g of 2-methylhexahydro-1H-azepine hydrochloride, and the mixture was stirred for 2 hours at 60° C. The reaction mixture was cooled to near room temperature, a saturated ammonium chloride aqueous solution was added therein, and the mixture was extracted with tert-butyl methyl ether three times. The organic layers were washed with a saturated sodium chloride aqueous solution, dried over anhydrous magnesium sulfate and concentrated. The residue was subjected to silica gel column chromatography to obtain 0.20 g of 1-(6-chloro-5-fluoropyrimidin-4-yl)-2-methylhexahydro-1H-azepine.

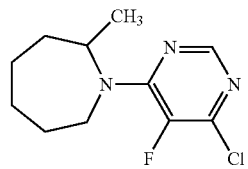

¹H-NMR: 1.17-1.50 (m, 6H involving a doublet at 1.18), 1.58-1.92 (m, 4H), 2.06-2.14 (m, 1H), 3.11 (t, 1H), 4.01 (brd, 1H), 4.57 (brs, 1H), 8.11 (s, 1H)

Formulation examples will be shown below. Parts are by weight.

Formulation Example 1

Each 9 parts of the present compounds (1) to (51) were dissolved in 37.5 parts of xylene and 37.5 parts of dimethylformamide, and to this was added 10 parts of polyoxyethylene styrylphenyl ether and 6 parts of calcium dodecylbenzenesulfonate, and they were mixed thoroughly to obtain a formulation.

Formulation Example 2

Each 9 parts of the present compounds (1) to (51) were dissolved in a mixture of 4 parts of sodium laurate, 2 parts of calcium ligninsulfonate, 20 parts of a synthetic water-containing silicon oxide fine powder, and 65 parts of diatomaceous earth, and they were mixed thoroughly to obtain a formulation.

Formulation Example 3

Each 3 parts of the present compounds (1) to (51) were dissolved in a mixture of 5 parts of a synthetic water-containing silicon oxide fine powder, 5 parts of sodium dodecylbenzeneuslfonate, 30 parts of bentonite, and 57 parts of clay, and they were mixed thoroughly, then, suitable amount of water was added to the mixture thereof, the resulted mixture was further stirred, granulated in a granulator, and dried under ventilation to obtain a formulation.

Formulation Example 4

Each 4.5 parts of the present compounds (1) to (51), 1 part of a synthetic water-containing silicon oxide fine powder, 1 part of DRILESS B (manufactured by Sankyo Co., Ltd.) and 7 parts of clay were mixed thoroughly in a mortar, then, stirred to mix by a juice mixer. To the resulted mixture was added 86.5 parts of cut clay, they were sufficiently stirred to mix, to obtain a formulation.

Formulation Example 5

Each 10 parts of the present compounds (1) to (51), 35 parts of white carbon containing 50 parts of ammonium polyoxyethylene alkyl ether sulfate, and 55 parts of water were mixed and finely ground according to a wet grinding method, to obtain a formulation.

Then, the effect of the present compound of controlling pests will be shown by test examples.

Test Example 1

A formulation of a test compound obtained in Formulation Example 5 was diluted with water so that the active ingredient concentration came to 500 ppm to prepare a test spray liquid.

The seeds of cucumber were planted in polyethylene cups and grown until their first foliage leaves developed, on which about 20 cotton aphids (*Aphis gossypii*) were made parasitic. After one day, the test spray liquid was sprayed at the rate of 20 ml/cup onto the cucumber plants. On the 6th day after the application, the number of cotton aphids was examined and the control value was determined by the following formula:

Control value (%)={1−(Cb×Tai)/(Cai×Tb)}×100 wherein the variables in the formula have the following meanings:

Cb: the number of insects before the treatment in the non-treated area;

Cai: the number of insects at the time of observation in the non-treated area;

Tb: the number of insects before the treatment in the treated area; and

Tai: the number of insects at the time of observation in the treated area.

As a result, the present compounds (1) to (8) and (10) to (55) had the control value of 90% or higher.

The comparative test was done with same way by using the compound of the formula (A):

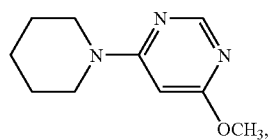

which is described in Tetrahedron Letters, No. 26, p. 3067-3070 (1968). The compound of the formula (A) had the control value of 29% or lower.

Test Example 2

A formulation of each test compound obtained according to Formulation Example 5 was diluted with water so that the active ingredient concentration came to 500 ppm to prepare a test spray liquid.

The seeds of cucumber were planted in a polyethylene cup, and grown until their first foliage leaves developed, and then a test spray liquid was applied at a ratio of 20 ml/cup to the plant. After the liquid sprayed to the cucumber were dried, the first true leaf was cut off and placed on a filter paper (70 mm in diameter) impregnated with water in a polyethylene cup (110 mm in diameter). Thirty larvae of Western flower thrips (*Frankliniella occidentalis*) were set free on the first true leaf, which was covered with a polyethylene cup. After seven days, the number of surviving pests was examined.

As a result, the number of surviving pests was 0 on the leaves treated with each of the present compounds (4), (8) to (11), (23), (24), (26), (29), (32), (33), (44), (46), (47), (51), (52) and (53).

Test Example 3

A formulation of each test compound obtained according to Formulation Example 5 was diluted with water to give the spray liquid for test wherein an effective ingredient concentration is 500 ppm.

The seeds of cabbage were planted in polyethylene cups and grown until their first foliage leaves developed. The first foliage leaves were left and the other leaves were cut off. Some adults of silverleaf whiteflies (*Bemisia argentifoli*) were set free on the cabbage plants and allowed to lay eggs for about 24 hours. The cabbage plants with about 80 to 100 eggs thus laid were left in a greenhouse for 8 days, and the above test spray liquid was sprayed at the rate of 20 ml/cup onto the cabbage plants with larvae being hatched from the laid eggs. On the 7th day after the application, the number of surviving larvae was counted.

As a result, for the present compounds (1) to (53), the number of surviving larvae on the cabbage leaves treated with each of these compounds was not greater than 10.

Test Example 4

A formulation of a test compound obtained in Formulation Example 5 was diluted with water so that the active ingredient concentration came to 500 ppm to prepare a test spray liquid.

Fifty grams of molding Bonsoru 2 (available from Sumitomo Chemical Co., Ltd.) was put into a polyethylene cup, and 10 to 15 seeds of rice were planted in the polyethylene cup. The rice plants were grown until the second foliage leaves developed and then cut into the same height of 5 cm. The test spray liquid, which had been prepared as described above, was sprayed at the rate of 20 ml/cup onto these rice plants. After the test liquid sprayed onto the rice plants was dried, thirty first-instar larvae of brown planthoppers (*Nilaparvata lugens*) were set free on the rice plants, which were then left in a greenhouse at 25° C. On the 6th day after the release of brown planthopper larvae, the number of brown planthoppers parasitic on the rice plants was examined.

As a result, in the treatment with each of the present compounds (2), (3), (6), (10) to (12), (14), (15), (17), (18), (22) to (26), (30), (31), (33) to (35), (41) to (43), (45) to (49) and (51), the number of parasitic insects on the 6th day after the treatment was not greater than 3.

Industrial Applicability

The present compound has an excellent ability of controlling pests, therefore, it is useful as an effective ingredient in a pests controlling composition.

The invention claimed is:
1. A pyrimidine compound of the formula (II′):

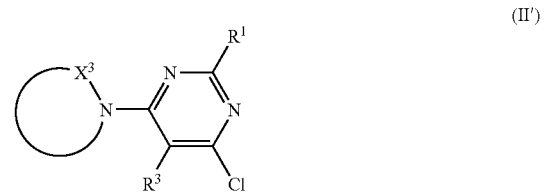

wherein $R^1$ represents a hydrogen atom, halogen atom or C1-C4 alkyl; $R^3$ represents a hydrogen atom, halogen atom or C1-C3 alkyl; $X^3$ represents C5 polymethylene, in which a single $CH_2$—$CH_2$ may be replaced with a single CH=CH, substituted with at least one substituent selected from the group consisting of halogen atoms, trifluoromethyl and C1-C4 alkyls.

2. The pyrimidine compound according to claim 1, wherein $X^3$ is C5 polymethylene substituted with at least one substituent selected from the group consisting of halogen atoms, trifluoromethyl and C1-C4 alkyls.

3. The pyrimidine compound according to claim 1, wherein $X^3$ is C5 polymethylene substituted with a halogen atom(s).

4. The pyrimidine compound according to claim 1, wherein $X^3$ is C5 polymethylene substituted with a trifluoromethyl.

5. The pyrimidine compound according to claim 1, wherein $X^3$ is C5 polymethylene substituted with a C1-C4 alkyl(s).

* * * * *